(12) United States Patent
Boutros et al.

(10) Patent No.: US 10,745,760 B2
(45) Date of Patent: Aug. 18, 2020

(54) BIOPSY-DRIVEN GENOMIC SIGNATURE FOR PROSTATE CANCER PROGNOSIS

(71) Applicants: ONTARIO INSTITUTE FOR CANCER RESEARCH (OICR), Toronto (CA); UNIVERSITY HEALTH NETWORK, Toronto (CA)

(72) Inventors: Paul Boutros, Toronto (CA); Robert G. Bristow, Toronto (CA); Emilie Lalonde, Toronto (CA)

(73) Assignees: University Health Network, Toronto (CA); Ontario Institute for Cancer Research, Toronto (CA)

( * ) Notice: Subject to any disclaimer, the term of this patent is extended or adjusted under 35 U.S.C. 154(b) by 484 days.

(21) Appl. No.: 15/112,110

(22) PCT Filed: Jan. 16, 2015

(86) PCT No.: PCT/CA2015/000026
§ 371 (c)(1),
(2) Date: Jul. 15, 2016

(87) PCT Pub. No.: WO2015/106341
PCT Pub. Date: Jul. 23, 2015

(65) Prior Publication Data
US 2016/0333421 A1 Nov. 17, 2016

Related U.S. Application Data

(60) Provisional application No. 61/928,444, filed on Jan. 17, 2014.

(51) Int. Cl.
| | |
|---|---|
| G01N 33/48 | (2006.01) |
| G01N 33/50 | (2006.01) |
| C12Q 1/6886 | (2018.01) |
| G16B 20/00 | (2019.01) |

(52) U.S. Cl.
CPC ........... *C12Q 1/6886* (2013.01); *G16B 20/00* (2019.02); *C12Q 2600/112* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS

| | | |
|---|---|---|
| 2007/0207478 A1 | 9/2007 | Paris et al. |
| 2009/0246781 A1 | 10/2009 | Klem et al. |
| 2013/0022974 A1 | 1/2013 | Chinnaiyan et al. |

FOREIGN PATENT DOCUMENTS

| | | |
|---|---|---|
| WO | WO 2006/052823 | 5/2006 |
| WO | WO 2012/149245 | 11/2012 |
| WO | WO 2013/003384 | 1/2013 |

OTHER PUBLICATIONS

Bristow et al., "OC-0139: Complementarity of genomic instability & hypoxia indices for predicting prostate cancer recurrence," *Radiotherapy and Oncology*, 111: XP029587279, (2015).
Fotouhi Ghiam et al., "Genomic Instability in Common Fragile Sites (CFSs) Is Associated with Less Favorable Outcome in Patients With Intermediate-Risk Prostate Cancer (IR-CaP)," *International Journal of Radation: Oncology Biology Physics*, 87(2): XP028725592, (2013).
Liu et al., "Comprehensive Assessment of DNA Copy Number Alterations in Human Prostate Cancers Using Affymetrix 100K SNP Mapping Array," *Genes, Chromosomes & Cancer*, 45: 1018-1032, (2006).
Office Communication issued in European Application No. 15737689. 8, dated Sep. 26, 2017.
Yu et al., "Genome Abnormalities Precede Prostate Cancer and Predict clinical Relapse," *Biomarkers, Genomics, Proteomics, and Gene Regulation*, 180(6): 2240-2248, (2012).
Zafarana et al., "Copy Number Alterations of c-MYC and PTEN Are Prognostic Factors for Relapse After Prostate Cancer Radiotherapy," *Cancer*, 118(16): 4053-4062, (2012).
International Search Report and Written Opinion issued in International Application No. PCT/CA2015/000026, dated May 1, 2015.
Search Report issued in European Patent Application No. 15737689. 8, dated Sep. 7, 2017.

*Primary Examiner* — Russell S Negin
(74) *Attorney, Agent, or Firm* — Norton Rose Fulbright US LLP

(57) ABSTRACT

There is provided herein, systems, devices and methods for determining a risk of recurrence of cancer following a cancer therapy of a patient by determining genomic instability of a tumour. There is further provided systems, devices and methods for categorizing a patient into a prognostic cancer sub-group by using copy number alterations.

13 Claims, 12 Drawing Sheets

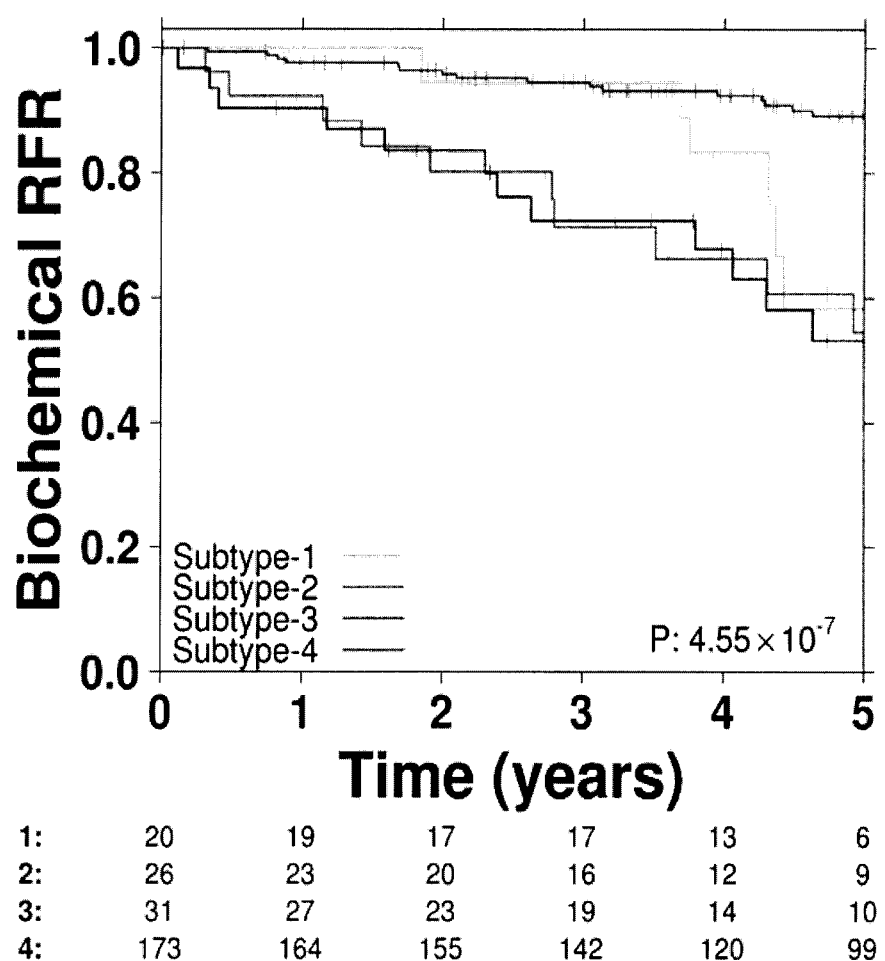

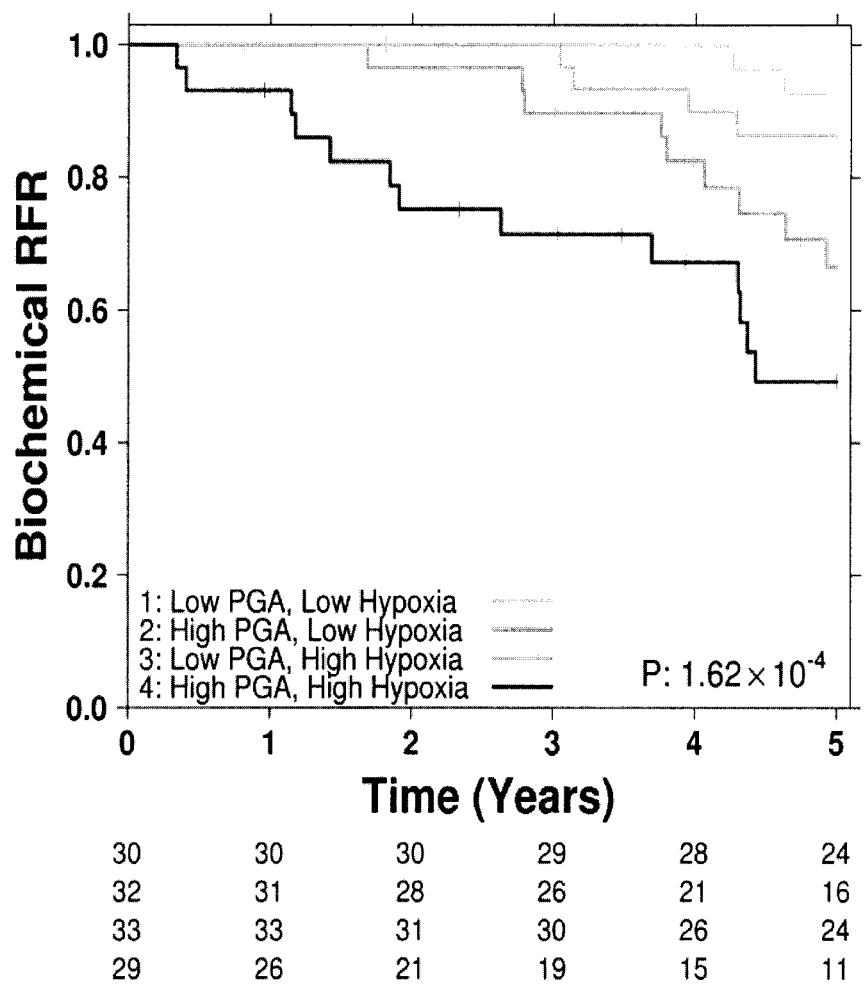

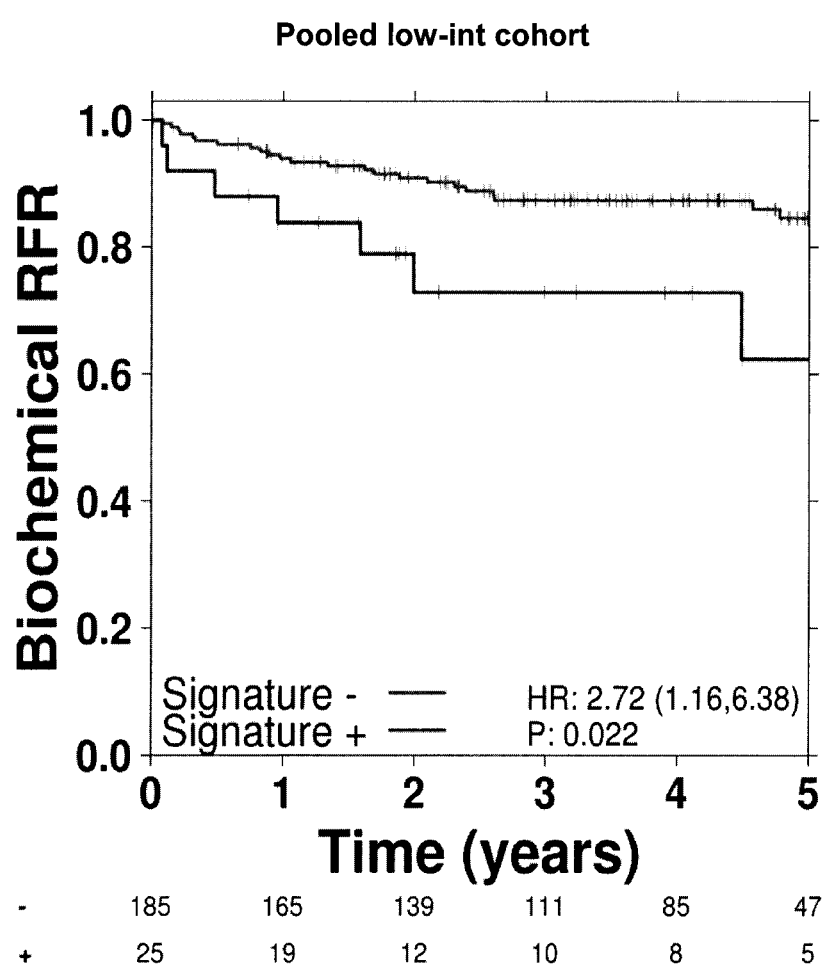

BIOPSY-DRIVEN GENOMIC SIGNATURE FOR PROSTATE CANCER PROGNOSIS

CROSS-REFERENCE TO RELATED APPLICATIONS

This application is a national phase application under 35 U.S.C. § 371 of International Application No, PCT/CA2015/000026 filed 16 Jan. 2015, which claims priority to U.S. Provisional Application No. 61/928,444 filed 17 Jan. 2014. The entire contents of each of the above-referenced disclosures is specifically incorporated by reference herein without disclaimer.

FIELD OF THE INVENTION

The present invention relates to methods for improved precision in prostate cancer patient prognosis using tumour biopsy-driven genomic signature profiles. Specifically, certain embodiments of the present invention relate to a method for determining a risk of recurrence of cancer following a cancer therapy of a patient, comprising determining genomic instability of a tumour of the patient.

BACKGROUND OF THE INVENTION

Prostate cancer (CaP) is the most common non-cutaneous malignancy in men and remains the second most common cause of male cancer deaths in North America. More than 90% of approximately 260,000 incident cases in North America present as localized disease. The prognosis of these cancers is stratified based on relative prostate-cancer specific mortality (PCSM) (e.g. low, intermediate and high-risk groups with hazard ratios for PCSM of approximately 1, 5 and 14, respectively) (D'Amico et al., 2003). These groupings are based on the levels of pre-treatment prostate-specific antigen (PSA), biopsy-based pathologic Gleason scores and UICC-TNM local and systemic staging descriptors. Many low risk patients can be offered active surveillance, sparing them the toxicities of radical treatment. High-risk patients often receive both local and systemic treatment in intensified protocols using radical prostatectomy (RadP) and/or image-guided radiotherapy (IGRT) combined with adjuvant androgen deprivation therapy (ADT) to offset the adverse impact of local failure and systemic occult metastases.

In contrast, the optimal treatment of the close to 75,000 North American men who present with non-indolent, intermediate-risk disease (e.g. highly similar Gleason scores of 6 or 7, PSA under 20 ng/mL and T1-T2N0M0) is an ongoing clinical dilemma (Shao et al., 2009). Up to one third of these patients undergo biochemical relapse, despite attempts at curative treatment using precision RadP or IGRT (Nichol, Warde, & Bristow, 2005). Furthermore, up to 12,000 (18%) of these patients fail within 18 months of primary therapy, and this heralds occult metastatic disease and increased PCSM (Buyyounouski, Pickles, Kestin, Allison, & Williams, 2012; Freedland et al., 2005; Johnson et al., 2013; Kapadia, Olson, Sandler, Feng, & Hamstra, 2012) As such, despite the use of clinical prognostic factors, intra- and inter-patient heterogeneity leads to clinical imprecision in the determination of which patients need treatment intensification a priori with ADT, chemotherapy or targeted therapies in order to prevent lethal castrate-resistant disease.

At present, no treatment-independent (e.g. useful for both IGRT and RadP patients), genome-wide signature exists to classify patients as potential responders or non-responders derived from initial diagnostic treatment biopsies. A pre-treatment, biopsy-based genomic signature reflecting tumour aggression could triage patients to intensified therapies and justify the additional toxicity to achieve cure in patient subgroups that are currently incurable by local therapy alone. Gene-specific studies have shown that copy number alterations (CNAs) in pre-treatment biopsies of PTEN, NKX3-1, MYC and the AR can associate with adverse prognosis in intermediate risk patients (Locke, Zafarana, Ishkanian, et al., 2012; Locke, Zafarana, Malloff, et al., 2012; Shen & Abate-shen, 2010; Zafarana et al., 2012). RNA-based gene signatures derived based on trans-urethral resections (TURP) or post-radical prostatectomy specimens (e.g. post-treatment) have been published which may differentiate between indolent and non-indolent prostate cancers ((J Cuzick et al., 2012; Jack Cuzick et al., 2011; Markert, Mizuno, Vazquez, & Levine, 2011; Penney et al., 2011; Wu et al., 2013). Surprisingly, and perhaps disappointingly, TMPRSS2:ERG fusion status is not associated with altered prognosis after either RadP (Minner et al., 2011) or IGRT (Dal Pra et al., 2013)). Finally, tumour cells do not exist within a homogenous microenvironment and intratumoural hypoxia has been linked to increased genetic instability, decreased DNA repair, decreased capacity for apoptosis, increased stress adaption including augmented autophagy, increased angiogenesis and increased metastatic potential (Bristow & Hill, 2008; Wouters & Koritzinsky, 2008). Indeed, prostate cancers harbouring hypoxic sub-regions are also aggressive and fail within the first 2 years (early failure) following IGRT or RadP (Milosevic et al., 2012; Turaka et al., 2012; Vergis et al., 2008). To date, there has not been any investigation or exploration of the potential interplay between genomic instability and hypoxia in the same tumour within the context of treatment outcome.

Low and intermediate risk cancers can be distinctly classified into subgroups based on their significant inter-patient genetic and microenvironmental heterogeneity in which some patients are extremely unlikely to fail therapy and others fail rapidly within 2 years of therapy. These translational outcome data, when combined with research findings that show that disparate CNA prognostic signatures can exist within foci of similar Gleason score (Boutros et al., 2013; Cooper, 2013), together sets the stage for aggressive ascertainment of both genomic and microenvironmental data prior to therapy. These novel combinatorial indices can be used to offer patients medical intensification and de-intensification strategies in the context of precision cancer medicine (Chin, Andersen, & Futreal, 2011; Tran et al., 2012).

SUMMARY OF THE INVENTION

In an aspect, there is provided a method for determining a risk of recurrence of cancer following a cancer therapy of a patient, comprising determining genomic instability of a tumour of the patient by: (a) obtaining a biopsy of the tumour; (b) identifying genome regions of the biopsy wherein the regions are at least loci rankings 1-45 of the 100-loci in Table 1; (c) determining a plurality of copy number calls in the genome regions; (d) intersecting the plurality of copy number calls with a reference gene list, to obtain a plurality of Copy Number Alterations (CNA) calls for each gene; (e) generating a CNA tumour profile based on the plurality of CNA calls; (f) comparing the CNA tumour profile to a reference profile of recurring cancer patients and a reference profile of nonrecurring cancer patients; (g) calculating a plurality of statistical distances between the CNA tumour profile and the reference profile of recurring cancer patients and the reference profile of nonrecurring cancer patients; wherein the statistical distance between the CNA tumour profile and the reference profile of recurring cancer patients and the reference profile of nonrecurring cancer patients is associated with the risk of cancer recurrence following the cancer therapy of the patient.

In another aspect, there is provided a method for categorizing a patient into a prognostic cancer sub-group comprising the steps of: (a) determining a plurality of copy number calls in 60% of the genome in a biopsy of a tumour of the patient; (b) intersecting the plurality of copy number calls with a reference gene list, to obtain a plurality of Copy Number Alternations (CNA) calls for each gene; (c) generating a CNA tumour profile based on the plurality of CNA calls; (d) calculating one or more statistical distances between the CNA tumour profile and a prognostic cancer sub-group CNA profile; and (e) assigning the patient having the CNA tumour profile to the prognostic cancer sub-group having the prognostic cancer sub-group CNA profile based on a smallest statistical distance between the CNA tumour profile and the prognostic cancer sub-group CNA profile; wherein each prognostic cancer sub-group is associated with a risk of failure of a cancer therapy.

In an aspect of the present invention, there is provided a method, performed by at least one computing device, for determining the risk of recurrence of cancer following a cancer therapy of a patient, comprising determining genomic instability of a tumour of the patient based on: (a) determining, at a processor, a genome of the tumour; (b) determining, by the processor, genome regions of the biopsy wherein the regions are at least loci rankings 1-45 of the 100-loci in Table 1; (c) determining, by the processor, a plurality of copy number calls in the genome regions; (d) determining, by the processor, a plurality of Copy Number Alternations (CNA) calls for each gene by intersecting the plurality of copy number calls with a reference gene list; (e) determining, by the processor, a CNA tumour profile based on the plurality of CNA calls; (f) determining, by the processor, a plurality of statistical distances between the CNA tumour profile and a reference profile of recurring cancer patients and a reference profile of nonrecurring cancer patients; wherein the statistical distance between the CNA tumour profile and the reference profile of recurring cancer patients and the reference profile of nonrecurring cancer patients is associated with a risk of cancer recurrence following the cancer therapy.

In yet another aspect of the present invention, a system for determining the risk of recurrence of cancer following a cancer therapy of a patient comprising determining genomic instability, the system comprising: a non-transitory computer readable storage medium that stores computer-readable code; a processor operatively coupled to the non-transitory computer readable storage medium, the processor configured to implement the computer-readable code, the computer-readable code configured to:
determine a genome of the tumour; determine genome regions of the biopsy wherein the regions are at least loci rankings 1-45 of the 100-loci in Table 1; determine a plurality of Copy Number Alterations (CNA) calls for each gene based on intersecting the copy number calls with a reference gene and storing the plurality of CNA calls in the non-transitory computer readable storage medium; determine a CNA tumour profile based on the plurality of CNA calls and storing the CNA tumour profile in a non-transitory computer readable storage medium; determine a plurality of statistical distances between the CNA tumour profile and a reference profile of recurring cancer patients and a reference profile of nonrecurring cancer patients;
wherein the statistical distance between the CNA tumour profile and the reference profile of recurring cancer patients and the reference profile of nonrecurring cancer patients is associated with a risk of cancer recurrence following the cancer therapy.

In yet another aspect, a method for categorizing a patient into a prognostic cancer sub-group, performed by at least one computing device, comprising: (a) receiving, at a processor, a selection of data comprising a plurality of copy number calls in 60% of the genome in a biopsy of a tumour of the patient; (b) determining, by the processor, a plurality of Copy Number Alterations (CNA) calls for each gene based on intersecting the copy number calls with a reference gene list stored in a database in a non-transitory computer readable storage medium; (c) generating, by the processor, a CNA tumour profile based on the plurality of CNA calls for each gene; (d) determining, by the processor, one or more statistical distances between the CNA tumour profile and a prognostic cancer sub-group CNA profile stored in a database in a non-transitory computer readable storage medium; (e) assigning, by the processor, the patient having the CNA tumour profile to the prognostic cancer sub-group having the prognostic cancer sub-group CNA profile based on a smallest statistical distance between the CNA tumour profile and the prognostic cancer sub-group CNA profile; wherein each prognostic cancer sub-group is associated with a risk of failure of a cancer therapy.

In an aspect of the present invention, a system for categorizing a patient into a prognostic cancer sub-group, the system comprising: a non-transitory computer readable storage medium that stores computer-readable code; a processor operatively coupled to the non-transitory computer readable storage medium, the processor configured to implement the computer-readable code, the computer-readable code configured to:
receive a selection of data comprising a plurality of copy number calls in 60% of the genome in a biopsy of a tumour of the patient; obtain a plurality of Copy Number Alterations (CNA) calls for each gene based on intersecting the plurality of copy number calls with a reference gene list stored in the non-transitory computer readable storage medium; generate a CNA tumour profile based on the CNA calls for each gene; determine one or more statistical distances between the CNA tumour profile and a prognostic cancer sub-group CNA profile stored in the non-transitory computer readable storage medium; assign the patient having the CNA tumour profile to the prognostic cancer sub-group having the prognostic cancer sub-group CNA profile based on a smallest statistical distance between the CNA tumour profile and the prognostic cancer sub-group CNA profile;
wherein each prognostic cancer sub-group is associated with a risk of failure of a cancer therapy.

BRIEF DESCRIPTION OF THE DRAWINGS

A detailed description of the preferred embodiments is provided herein below by way of example only and with reference to the following drawings, in which:

FIG. 1, which illustrates the 4 genetically distinct subgroups of low to intermediate risk prostate tumours fom the Toronto and MSKCC cohorts. FIG. 1B shows the genomic subtypes, having significantly different biochemical relapse rates.

FIG. 3, which shows hypoxia in the IGRT cohort. FIG. 3E shows PGA and hypoxia have a synergistic prognostic effect in the Toronto-IGRT cohort.

FIG. 4, which shows the prognosis of a CNA-based gene signature. Specifically, FIG. 4A shows that the signature which was developed with the IGRT cohort can identify low- to intermediate-risk pooled RadP patients (MSKCC and Cambridge cohorts) at significantly higher risk of biochemical relapse.

Figure 1A:
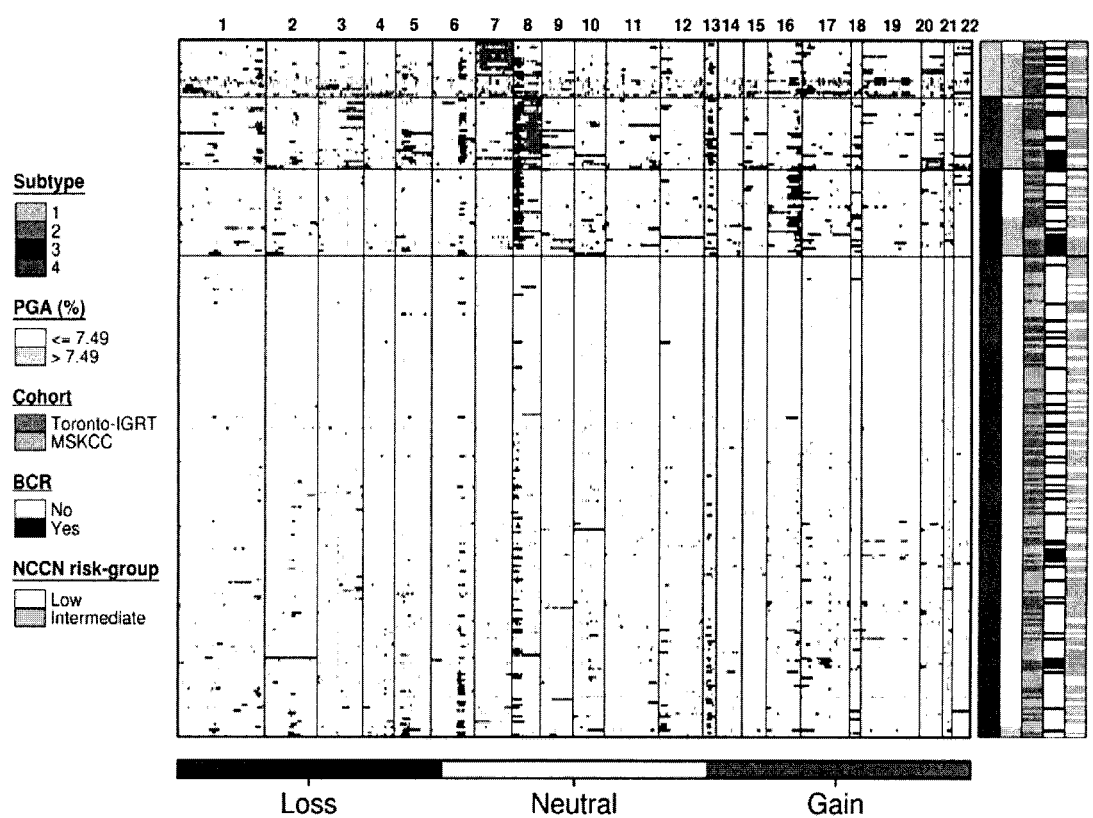
FIG. 1A shows the copy number landscape of the four distinct genomic subtypes with key covariates shown on the right.

In the drawings, preferred embodiments of the invention are illustrated by way of example. It is to be expressly understood that the description and drawings are only for the purpose of illustration and as an aid to understanding, and are not intended as a definition of the limits of the invention.

DETAILED DESCRIPTION OF THE INVENTION

Despite tight prognostic groupings, localized prostate cancers are still clinically heterogeneous as 30-50% of patients recur after local treatment with image-guided radiotherapy or radical prostatectomy. Using machine learning approaches with aCGH data derived from pre-treatment prostate biopsies (training set) and two clinically-similar cohorts (validation sets), we show that inter-patient heterogeneity can be further defined by combined indices of the tumour-microenvironment (hypoxia), genomic instability and gene-specific molecular aberrations. Specific genetic subtypes and genomic instability were found to be novel independent factors associated with biochemical relapse; an effect magnified by intra-tumoural hypoxia. Furthermore, classification of 75% of patients as low- or high-risk for treatment failure was achieved using a novel 100-locus signature. This is the first cancer outcome study to integrate DNA- and microenvironment-based failure indices to robustly predict patient outcome. Patients exhibiting these aggressive features on biopsy should be entered into treatment intensification trials.

In an aspect, there is provided a method for determining a risk of recurrence of cancer following a cancer therapy of a patient, comprising determining genomic instability of a tumour of the patient by: (a) obtaining a biopsy of the tumour; (b) identifying genome regions of the biopsy wherein the regions are at least loci rankings 1-45 of the 100-loci in Table 1; (c) determining a plurality of copy number calls in the genome regions; (d) intersecting the plurality of copy number calls with a reference gene list, to obtain a plurality of Copy Number Alterations (CNA) calls for each gene; (e) generating a CNA tumour profile based on the plurality of CNA calls; (f) comparing the CNA tumour profile to a reference profile of recurring cancer patients and a reference profile of nonrecurring cancer patients; (g) calculating a plurality of statistical distances between the CNA tumour profile and the reference profile of recurring cancer patients and the reference profile of nonrecurring cancer patients; wherein the statistical distance between the CNA tumour profile and the reference profile of recurring cancer patients and the reference profile of nonrecurring cancer patients is associated with the risk of cancer recurrence following the cancer therapy of the patient.

As used herein, "genomic instability" is the degree of genetic differences that exist between a reference genetic baseline and a genetic sample. The genetic differences that exist may be expressed by proxy with specific reference to the number of copy number calls made between the reference genetic baseline and the genetic sample.

As used herein, "locus" is a specific genetic region of variable length and identity. A ranking of a selection of relevant loci is found in Table 1.

As used herein, "copy number call" is the quantity of a genetic unit obtained from a genetic sample subjected to a genetic assay. Copy number calls may be assessed thorough the use of an amplified fragment pool assay, as described more fully below.

As used herein, "copy number alteration", or CNA, is the value representing a comparison of the copy number call of a given genetic unit to that of a reference genome that may give rise to a determination as to whether there is a loss or gain of genetic material for that given genetic unit.

As used herein, "CNA tumour profile" is the plurality of CNAs associated with a given genetic tumour sample.

As used herein, "reference profile of recurring cancer patients" is the plurality of CNAs associated with a given set of genetic tumour samples of a population of patients wherein it is known that cancer reoccurred after a given cancer treatment.

As used herein, "reference profile of nonrecurring cancer patients" is the plurality of CNAs associated with a given set of genetic tumour samples of a population of patients wherein it is known that cancer did not reoccur after a given cancer treatment.

As used herein, "statistical distance" is a value representing the comparison of sets of data that gives rise to a determination of the degree of association, or lack thereof, between said sets of data. A specific embodiment of a statistical distance may be the use of a Jaccard distance (Jaccard, 1901), as described more fully below.

In an embodiment, the genome regions are at least loci rankings 1-50, 1-60, 1-70, 1-80, 1-90 or 1-100 in Table 1.

In an embodiment, the genome regions are a whole tumour genome.

In some embodiments, the patient has been diagnosed with prostate cancer. In some instances, the patient has been diagnosed with localized prostate cancer. Preferably, the patient has one of a low or intermediate risk for prostate cancer. For example, the patient has one of a low or intermediate risk for prostate cancer as determined by at least one of T-category, Gleason score or pre-treatment prostate-specific antigen blood concentration.

Classifying a patient as being at low, intermediate or high risk for prostate cancer mortality is well understood by a person skilled in the art. For example, there are five common classification systems used to clinically stratify prostate cancer patients into low, intermediate or high risk groups: NCCN, D'Amico, GUROC, CAPSURE and ESMO (see Table 7). Each of these will stratify prostate cancer patients as low, intermediate or high risk based on Gleason score, pre-treatment PSA and T-category. The Gleason score is obtained from the diagnostic biopsy, and determined by a pathologist. The T-category is related to the size and spread of the tumour within the prostate and surrounding area, as determined by a digital rectum exam and imaging tests. PSA is a blood-based biomarker, measured in ng/mL.

In some embodiments, the low risk for prostate cancer is determined by at least one of the following: (a) a T-category of T1-T2a, a Gleason score less than or equal to 6, and a pre-treatment prostate-specific antigen blood concentration less than or equal to 10 ng/mL; (b) a T-category of T1-T2a, a Gleason score greater than or equal to 2 and less than or equal to 6, and a pre-treatment prostate-specific antigen blood concentration less than or equal to 10 ng/mL; and (c) a T-category of T1c, a Gleason score less than or equal to 6, a pre-treatment prostate-specific antigen blood concentration less than or equal to 10 ng/mL, and fewer than 3 biopsy cores of a tumour that are positive for cancer and having less than or equal to 50% cancer in each.

In some embodiments, the intermediate risk for prostate cancer is determined by at least one of the following: (a) at least one of a T-category of T2b, a Gleason score equal to 7, and a pre-treatment prostate-specific antigen blood concentration greater than 10 ng/mL; (b) at least one of a T-category of T1-T2, a Gleason score equal to or less than 7, and a pre-treatment prostate-specific antigen blood concentration less than or equal to 20 ng/mL; (c) at least one of a T-category of T2b, a Gleason score equal to 7 and a pre-treatment prostate-specific antigen blood concentration greater than 10 ng/ml and equal to or less than 20 ng/mL; and (d) at least one of a T-category of T2b, a T-category of T2c, a Gleason score equal to 7 and a pre-treatment prostate-specific antigen blood concentration greater than 10 ng/ml and equal to or less than 20 ng/mL.

In another aspect, there is provided a method for categorizing a patient into a prognostic cancer sub-group comprising the steps of: (a) determining a plurality of copy number calls in 60% of the genome in a biopsy of a tumour of the patient; (b) intersecting the plurality of copy number calls with a reference gene list, to obtain a plurality of Copy Number Alternations (CNA) calls for each gene; (c) generating a CNA tumour profile based on the plurality of CNA calls; (d) calculating one or more statistical distances between the CNA tumour profile and a prognostic cancer sub-group CNA profile; and (e) assigning the patient having the CNA tumour profile to the prognostic cancer sub-group having the prognostic cancer sub-group CNA profile based on a smallest statistical distance between the CNA tumour profile and the prognostic cancer sub-group CNA profile; wherein each prognostic cancer sub-group is associated with a risk of failure of a cancer therapy.

As used herein, a "prognostic cancer subgroup" is one of a plurality of populations stratified according to genetic identity, each subgroup associated with a specific prognostic outcome associated with cancer. For example, specific embodiments of prognostic cancer subgroups may be the genetic subtypes as expressed in FIG. 1 and Tables 3, 4 and 5.

In an embodiment, the plurality of copy number calls is determined in at least one of 70%, 80%, 90%, 95% or 100% of the genome of the tumour.

In an embodiment, the statistical distance is a Jaccard distance.

In some embodiments, the patient has been diagnosed with prostate cancer. In some instances, the patient has been diagnosed with localized prostate cancer. Preferably, the patient has one of a low or intermediate risk for prostate cancer. For example, the patient has one of a low or intermediate risk for prostate cancer as determined by at least one of T-category, Gleason score or pre-treatment prostate-specific antigen blood concentration.

In some embodiments, the biopsy is obtained before the cancer therapy.

In some embodiments, the cancer therapy comprises treatment of the patient with at least one of image-guided radiotherapy or radical prostatectomy.

In some embodiments, the method further comprises determining hypoxia levels of the tumour.

In an aspect of the present invention, there is provided a method, performed by at least one computing device, for determining the risk of recurrence of cancer following a cancer therapy of a patient, comprising determining genomic instability of a tumour of the patient based on: (a) determining, at a processor, a genome of the tumour; (b) determining, by the processor, genome regions of the biopsy wherein the regions are at least loci rankings 1-45 of the 100-loci in Table 1; (c) determining, by the processor, a plurality of copy number calls in the genome regions; (d) determining, by the processor, a plurality of Copy Number Alternations (CNA) calls for each gene by intersecting the plurality of copy number calls with a reference gene list; (e) determining, by the processor, a CNA tumour profile based on the plurality of CNA calls; (f) determining, by the processor, a plurality of statistical distances between the CNA tumour profile and a reference profile of recurring cancer patients and a reference profile of nonrecurring cancer patients; wherein the statistical distance between the CNA tumour profile and the reference profile of recurring cancer patients and the reference profile of nonrecurring cancer patients is associated with a risk of cancer recurrence following the cancer therapy.

In yet another aspect of the present invention, a system for determining the risk of recurrence of cancer following a cancer therapy of a patient comprising determining genomic instability, the system comprising: a non-transitory computer readable storage medium that stores computer-readable code; a processor operatively coupled to the non-transitory computer readable storage medium, the processor configured to implement the computer-readable code, the computer-readable code configured to:
    determine a genome of the tumour; determine genome regions of the biopsy wherein the regions are at least loci rankings 1-45 of the 100-loci in Table 1; determine a plurality of Copy Number Alterations (CNA) calls for each gene based on intersecting the copy number calls with a reference gene and storing the plurality of CNA calls in the non-transitory computer readable storage medium; determine a CNA tumour profile based on the plurality of CNA calls and storing the CNA tumour profile in a non-transitory computer readable storage medium; determine a plurality of statistical distances between the CNA tumour profile and a reference profile of recurring cancer patients and a reference profile of nonrecurring cancer patients;
wherein the statistical distance between the CNA tumour profile and the reference profile of recurring cancer patients and the reference profile of nonrecurring cancer patients is associated with a risk of cancer recurrence following the cancer therapy.

In yet another aspect, a method for categorizing a patient into a prognostic cancer sub-group, performed by at least one computing device, comprising: (a) receiving, at a processor, a selection of data comprising a plurality of copy number calls in 60% of the genome in a biopsy of a tumour of the patient; (b) determining, by the processor, a plurality of Copy Number Alterations (CNA) calls for each gene based on intersecting the copy number calls with a reference gene list stored in a database in a non-transitory computer readable storage medium; (c) generating, by the processor, a CNA tumour profile based on the plurality of CNA calls for each gene; (d) determining, by the processor, one or more statistical distances between the CNA tumour profile and a prognostic cancer sub-group CNA profile stored in a database in a non-transitory computer readable storage medium; (e) assigning, by the processor, the patient having the CNA tumour profile to the prognostic cancer sub-group having the prognostic cancer sub-group CNA profile based on a smallest statistical distance between the CNA tumour profile and the prognostic cancer sub-group CNA profile; wherein each prognostic cancer sub-group is associated with a risk of failure of a cancer therapy.

In another aspect of the present invention, a system for categorizing a patient into a prognostic cancer sub-group, the system comprising: a non-transitory computer readable storage medium that stores computer-readable code; a processor operatively coupled to the non-transitory computer readable storage medium, the processor configured to implement the computer-readable code, the computer-readable code configured to:
receive a selection of data comprising a plurality of copy number calls in 60% of the genome in a biopsy of a tumour of the patient; obtain a plurality of Copy Number Alterations (CNA) calls for each gene based on intersecting the plurality of copy number calls with a reference gene list stored in the non-transitory computer readable storage medium; generate a CNA tumour profile based on the CNA calls for each gene; determine one or more statistical distances between the CNA tumour profile and a prognostic cancer sub-group CNA profile stored in the non-transitory computer readable storage medium; assign the patient having the CNA tumour profile to the prognostic cancer sub-group having the prognostic cancer sub-group CNA profile based on a smallest statistical distance between the CNA tumour profile and the prognostic cancer sub-group CNA profile;
wherein each prognostic cancer sub-group is associated with a risk of failure of a cancer therapy.

The present invention will be understood by reference to the following non-limiting examples:

EXAMPLES

Materials and Methods
Toronto-IGRT cohort (Training Set)

As previously described (Ishkanian et al., 2009), a cohort of 247 men with histologically confirmed adenocarcinoma of the prostate were studied in a prospective clinical study, which was approved by the University Health Network Research Ethics Board and registered (NCT00160979) in accordance with the criteria outlined by the International Committee of Medical Journal Editors. Briefly, from 1996-2006, flash-frozen, pre-treatment biopsies were derived from those patients who had chosen radical IGRT for primary treatment. The clinical target volume (CTV) encompassed the prostate gland alone. The planning target volume (PTV) was defined by a 10 mm margin around the CTV except posteriorly where the margin was 7 mm. All patients were treated with 6-field conformal or intensity modulated radiotherapy using fiducial gold seeds for daily set-up and quality assurance to preclude geographical misses. The radiotherapy dose was escalated over the period of accrual in a series of separate phase I/II studies.

There was sufficient tumour in the biopsies of 142 of these patients to permit microdissection. Of these 142 patients, 126 patients had information pertaining to long-term biochemical outcome and were treated with IGRT as previously described. The final cohort therefore included 126 patients, of which 47 had biochemical relapse. Patients were followed at 6 monthly intervals after completing treatment with clinical examination and PSA. Additional tests and the management of patients with recurrent disease were at the discretion of the treating physician. The median follow-up of surviving patients was 7.8 years following the end of treatment.

Measurement of Focal Tumour Hypoxia in Toronto-IGRT Cohort (HP20 Index)

Intra-glandular measurements of pO2 to define individual prostate cancer hypoxia was measured pre-radiotherapy for all patients in the IGRT using an ultrasound-guided transrectal needle-piezoelectrode technique (Milosevic et al., 2012). Between forty to eighty individual oxygen readings were obtained along 2 to 4 linear measurement tracks 1.5 to 2 cm in length through regions of the prostate likely to contain tumour (based on real-time Doppler ultrasound, digital rectal examination and previous diagnostic biopsies). Patients were awake throughout and local anesthetic was not used. Tumour needle biopsies were then obtained along the measurement tracks for correlative molecular studies. The flash frozen biopsies used for aCGH analyses were therefore obtained from the same spatial locale as the pO2 measurements. All oxygen measurements (excluding nonphysiologic values <3 or >100 mm Hg) along all tracks were included in the analyses. The percentage of pO2 oxygen measurements less than 20 mm Hg (e.g. HP20) was selected as the independent variable for all analyses investigating relationships between genomic instability and hypoxia.

aCGH Analysis

Frozen biopsies were embedded in optimum cutting temperature (OCT) at −80° C. and cut into 10-micron sections for manual microdissection and preparation of DNA samples as previously described (Ishkanian et al., 2009). Briefly, 300 ng of tumour and reference DNA were differentially labeled with Cyanine 3-dCTP and Cyanine 5-dCTP (Perkin Elmer Life Sciences). The samples were then applied onto whole genome tiling path arrays containing 26,819 bacterial artificial chromosome (BAC)-derived amplified fragment pools spotted in duplicate on aldehyde coated glass slides (SMIGRT v.2, BC Cancer Research Centre Array Facility, Vancouver). The log 2 ratios of the Cyanine 3 to Cyanine 5 intensities for each spot were assessed. Data were filtered based on both standard deviations of replicate spots (data points with greater than 0.075 standard deviation were removed) and signal to noise ratio (data points with a signal to noise ratio less than 3 were removed).

The resulting dataset was normalized using a stepwise normalization procedure (Khojasteh, Lam, Ward, & MacAulay, 2005). The genomic positions of clones are mapped to the NCBI's Genome Build 36.1, released in March 2006. Areas of aberrant copy number were identified using a robust Hidden Markov Model (Shah et al., 2006) and classified as either loss, neutral or gain for all probes processed. The liftOver tool from UCSC was used to map the copy number segments to the hg19 human genome build. Fragments overlapping centromeres, telomeres or other gaps in the hg18 build were trimmed conservatively (regions were shortened rather than elongated). To generate contiguous CNA regions, probe-based CNA calls were collapsed with neighbouring probes within the same chromosome with the same copy number. CNA regions with only one supporting probe were filtered. In addition, any CNAs found in centromeres or telomeres, as defined by the UCSC gap table, were removed. CNA regions were intersected with gene annotation to generate gene-based CNA calls. This gene list was further filtered to match the published gene list from the MSKCC cohort.

MSKCC Radical Prostatectomy (RadP) Cohort (Validation Set)

To validate signatures, published data from a cohort of 250 patients treated by radical prostatectomy at the Memorial Sloan Kettering Cancer Center was mined using the Cancer Genomics cBioPortal (Taylor et al., 2010). We selected clinically-staged T1-T2N0M0 primary tumours and classified patients as low, intermediate and high-risk, according to NCCN guidelines (Mohler et al., 2012). Normalized and segmented data was downloaded from cBioPortal. Patient DNA had been hybridized to Agilent's 244k platform generating ~244,000 tumour to normal DNA intensity ratios. The normal samples used in this study were matched DNA when available or else pooled normal DNA. The segmented data consisted of regions of similar copy number status and a log-ratio. Thresholds of $<-0.2$ and $>0.2$ were used to define deletions and amplifications, respectively. Again, the copy number fragments were mapped to the hg19 human reference build using the liftOver tool, and filtered as above for the IGRT cohort. This data was used to calculate PGA (see below). We also downloaded the output of RAE, providing genes in regions of copy number per patient as described in the original publication by Taylor and colleagues. CNA calls were collapsed from $\{-2, -1, 0, 1, 2\}$ to $\{-1, 0, 1\}$. The median follow-up time for this cohort was 4.6 years, with 19 of 124 patients experiencing biochemical recurrence.

Cambridge RadP Cohort (Validation Set)

To further validate our prognostic indices, we obtained a second RadP cohort consisting of 117 low-high risk men treated in the UK (unpublished data; Ross-Adams et al.). Ethical approval for the use of samples and data collection was granted by the local Research Ethics Committee under ProMPT (Prostate Mechanisms for Progression and Treatment) 'Diagnosis, investigation and treatment of prostate disease' (MREC 01/4/061). The Cambridge cohort comprises matched tumour and benign tissues from 117 men with histologically-confirmed prostate cancer at radical prostatectomy. Samples were prepared as previously described, and the minimum inclusion threshold for the percentage of tumour in samples was 40% (Warren, 2013). Comprehensive clinical (diagnostic) data were collected, including pre-operative and follow-up PSA, TNM staging, and Gleason score. The average age was 61 years (range 41-73). The median time to biochemical relapse is 2.8 years, and as such we focus on 18 month bRFR for this cohort when used alone. Given 26 events in this cohort and a 0.05 probability of a type I error, we have power of 0.42 and 0.80 to detect a hazard ratio of 2.0 and 3.0, respectively.

Total genomic DNA and mRNA RNA was extracted from each tumour and benign tissue core (Qiagen AllPrep). Copy number variation was assayed with Illumina HumanOmni2.5-8 bead chip arrays (Aros Applied Biotechnology, Aarhus, Denmark) and pre-processed using OncoSNP (Yau, 2010). OncoSNP ranks the copy number calls from 1 (most confident, typically larger) to 5 (least confident, typically smaller); see https://sites.google.com/site/oncosnp/user-guide/interpreting-oncosnp-output for details. We accepted copy number calls of rank 3 or less in order to include both broad and focal CNAs. Expression profiling was performed on Illumina HT12 arrays. Bead level data were pre-processed to remove spatial artifacts, $log_2$-transformed and quantile normalized using the beadarray package in Bioconductor prior to analysis (Dunning, 2007). The ComBAT method, as implemented in the sva Bioconductor package (v3.2.1), was used to address batch effects in the expression data (Johnson, 2007). To collapse the expression data to gene level, the probe with the largest inter-quartile range was used to represent each gene.

RNA Hypoxia Signatures

To evaluate hypoxia in the MSKCC and Cambridge cohorts, we used three previously published mRNA signatures for hypoxia (Buffa 2010; Eustace 2013; Winter 2007). The gene signatures were applied to 108/154 MSKCC patients and 110/117 Cambridge patients with mRNA data available. To generate hypoxia scores, each gene in each patient was evaluated against the median gene abundance for the same gene within the cohort. Patients with abundance greater than the median received a gene score of 1, and patients with abundance lower than the median received a gene score of $-1$. The hypoxia RNA score for a patient is the sum of the gene-scores for each gene in a signature.

The RNA Hypoxia Scores were median dichotomized to define low- or high-hypoxia tumours. This was repeated for all three hypoxia signatures. These signatures have not been evaluated in prostate cancer. Validation in prostate cancer is required to illustrate that they are indeed measuring tumour hypoxia. Nonetheless, we used these promising signatures as a proxy for tumour hypoxia for the first time in prostate cancer, which was later validated by our results from the IGRT cohort, in which we have direct intra-glandular hypoxia measurements at the site of biopsy.

Statistical Methods

Clinical risk groups were determined using the NCCN classification system (Mohler et al., 2012). The primary outcome was time to biochemical failure as defined by Roach et al. to be a PSA rise of at least 2 ng/mL above post-radiation nadir value for RT patients, or PSA concentration $<0.2$ after RadP (Roach et al., 2006). Five-year biochemical relapsed free rates (RFR) rates were calculated using the Kaplan-Meier method. Cox proportional hazard models were fit when possible, adjusting for Gleason score and PSA levels. T status was not prognostic within the low-intermediate risk patients in either cohort. PSA was thus not used in the models, except when using all risk groups where PSA, T status and Gleason scores were all included. Proportional hazard assumptions were tested with the R function cox.zph. If a variable failed these assumptions, the variable was either stratified (e.g. for PSA) or a log-rank test was used.

Receiver operator characteristic (ROC) and C-index analyses were performed with the survivalROC (v1.0.3) and Hmisc (3.14-4) packages, respectively. We used the survivaIROC package to perform ROC analysis while accounting for data censoring, using Nearest Neighbour Estimation with default parameters at a prediction time of 18 months and 5 years (Heagerty, Lumley, & Pepe, 2000). In the univariate setting, the biomarkers were used as the predictor variable for ROC and C-index analyses. In the multivariate setting, we used the output of coxph models which include both the biomarker of interest and relevant clinical factors (PSA and Gleason score for low-int models, and PSA, Gleason score, and T category for full models). All statistical analyses were done in the open source R software versions 3.0.2 using the survival package version 2.37-4. A two-sided p-value of 0.05 was used to assess statistical significance and the false-discovery rate or the Bonferroni correction was applied to correct for multiple testing, where appropriate.

Cohort Comparison

We used several subsets of the validation cohorts in our analyses. To clinically match the IGRT/training cohort, we focused on the patients with low or intermediate risk disease ('Low+Int', n=124 for MSKCC and n=86 for Cambridge). To increase power and to verify prognosis in a more diverse cohort, we also considered the full cohort which consists of an additional 30 high-risk MSKCC patients, 26 high-risk Cambridge patients, and 5 Cambridge patients with unknown classification ('Full', n=271). Finally, to evaluate the RNA hypoxia signatures (above) and to compare our DNA-based signature to prognostic RNA indices (below), we considered the subset of 271 RadP patients with information on both mRNA and CNA (n=108 for MSKCC and n=110 for Cambridge).

Unsupervised Hierarchical Clustering

To find the optimal number of subtypes, the R package ConsensusClusterPlus (Sebastiani, Kohane, & Ramoni, 2003) was used with 80% subsampling on the IGRT dataset for 1000 iterations, with a maximum number of subtypes set to 15. Ward clustering with Jaccard distance (Jaccard, 1901) was used to subtype patients. ConsensusClusterPlus also determines the subtype assignment for each patient. The profile of each subtype was defined as the median CN of each gene, rounded to the nearest copy number. Patients from the RadP cohort were assigned to the subtype which had the most similar CN profile (based on the Jaccard distance metric).

The distribution of several variables of interest was compared across the four subtypes. For the categorical variables (Gleason score, T status, BCR status, BCR status at 18 months, discretized hypoxia, ERG and risk group), a deviance test was conducted to determine whether there was a statistically significant interaction between each variable and the clustering. For the continuous variables (PSA, PGA), we conducted a Kruskal-Wallis test to compare the distribution of each variable across the four subtypes. These tests were repeated for both cohorts combined and for each cohort separately.

Percent Genome Alteration (PGA)

Percentage Genome Alteration was calculated in the IGRT cohort in the following way: each region of copy number alteration was identified and defined by length of each gain or loss across the genome in base pairs. The cumulative number of base pairs altered was calculated by adding all regions of alteration per patient. The total number of base pairs altered was divided by the number of base pairs covered on the array to provide a percentage of each patient's genome altered. PGA was treated as a continuous variable for multi-parameter modeling, but dichotomized at the median for presentation in univariate KM curve analyses.

Interaction Between Percent Genome Alteration and Hypoxia

A Cox proportional hazard regression model with an interaction term between PGA and hypoxia was used to test for a synergistic effect between the two variables. Both variables were median dichotomized to define patients with low vs. high values. For hypoxia, we used three previously published RNA signatures in the RadP cohorts (Best, Buffa, and West signatures) and HP20 (which is a direct measurement of intra-tumour $pO_2$, see above) in the Toronto-IGRT cohort.

100-Loci DNA Gene Signature

A random forest (Breiman, 2001) with 1 million trees was trained with the IGRT cohort and validated with the RadP cohort to identify a gene signature. Given copy number status per patient (−1, 0 or 1), the random forest predicts the occurrence of BCR for each patient. To eliminate redundancy, neighbouring genes with identical copy numbers across all patients from both cohorts were collapsed into a single feature. This reduced our feature set by ~3-fold, resulting in 5,355 collapsed features. Signature sizes of 1, 5, 10, 30, 50, 75, 100, 300, 500 and 1000 features were tested with a leave-one-out cross-validation approach. To select which genes to include in a signature, (i.e. attempt to find the most informative genes in predicting BCR), a binomial logistic regression model was fit to each feature and features were selected by p-value. The optimal gene signature size (100 features) was used to train the entire IGRT cohort and was validated with both RadP cohorts. Variable importance was assessed with the Gini score and by the variable importance information generated from random forest training. The gene signature is obtained by mapping the selected collapsed features back to individual genes. The Signature Risk Score is the predicted score from the random forest (i.e. the proportion of trees that voted 'yes', where a 'yes' vote means the tree predicts that the patient will have biochemical relapse).

A bootstrap analysis was performed to evaluate how the identified signature compares to an empirical null distribution, as previously described (Boutros 2009; Starmans 2011). A null distribution was created by generating 1 million random sets of 100 features (sampled from the 5,355 collapsed regions) and repeating the random forest training and classification with the IGRT and pooled RadP cohorts, respectively. For each random gene set, the AUC and c-index of that model in the pooled RadP cohorts were obtained.

Comparison of Genomic Prognostic Signatures

We compared the AUC of our 100-loci DNA signature to 23 previously published RNA-based prognostic signatures for BCR in prostate cancer. To enable a fair comparison between the DNA and RNA signatures, we trained the RNA signatures with random forests, and tested their performance on the same subset of the MSKCC cohort. In total, 108 MSKCC patients with localized disease have mRNA and CNA information. To train the models with the RNA signatures, the GenomeDX prostate cancer database was used, which contains genome-wide mRNA abundance values from microarrays for primary tumour samples from the Mayo Clinic (Erho 2013; Karnes 2013), Cleveland Clinic (Magi-Galluzzi 2013), Thomas Jefferson University (Den 2013), New York University, Moffit Cancer Center, Erasmus Medical Center (Boormans 2013), Institute of Cancer Research (Jhavar 2009), and MSKCC (Taylor 2010). All patients from the GenomeDX database except for the MSKCC patients were used to train two models for each signature: one using only low and intermediate risk patients, and another using low- to high-risk patients, including some patients with node-positive disease. This results in a training set of 293 patients for the low-intermediate risk patient models, and of 1299 patients for the full-cohort patient models. The methodology for the low-intermediate risk cohort and the low-high risk cohort are the same, with each model producing a set of predictions scores and AUCs, implemented in R (version 2.15.3).

Every patient sample was normalized using SCAN at the probe selection region (PSR) level (v1.0.0, customized for the HuEx arrays) (Piccolo 2013). Each gene in the signatures was summarized by taking the median expression of any PSR which falls within an exon of the gene. In the rare event that no PSR and exon overlap, intronic PSRs were used instead. If no PSR was found within the gene's genomic region, the gene was not included in the remodeled signature. All samples, excluding MSKCC, were used for training a random forest classifier randomForest package v 4.6-7) to predict biochemical relapse. Tuning of the classifier's parameters was done using a 5 by 5 grid search of the mtry and nodesize parameters. The best tuning parameters were selected after a 10-fold cross validation performance evaluation. Each tuned model was applied to the MSKCC patients to produce a risk score between 0-1 for the patient's likelihood of biochemical progression.

Figure 4B:
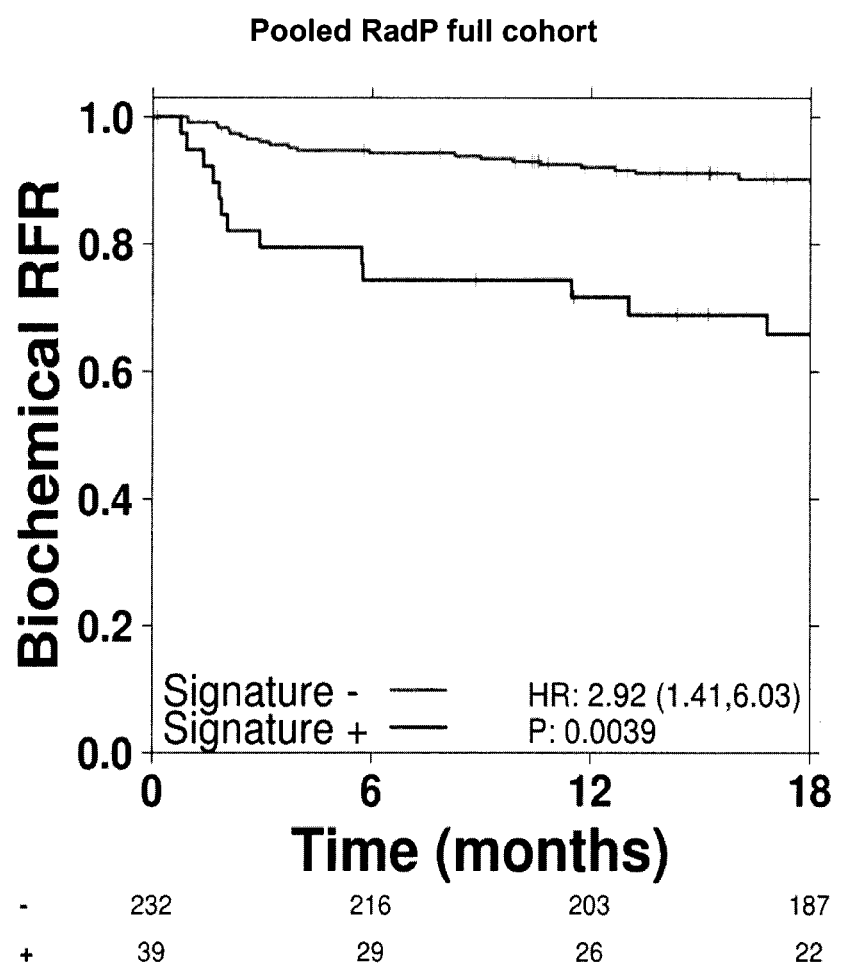
FIG. 4B demonstrates that the signature is capable of identifying patients that will fail rapidly (<18 months) when considering all risk groups from the pooled RadP cohort. Finally.
Figure 4C:
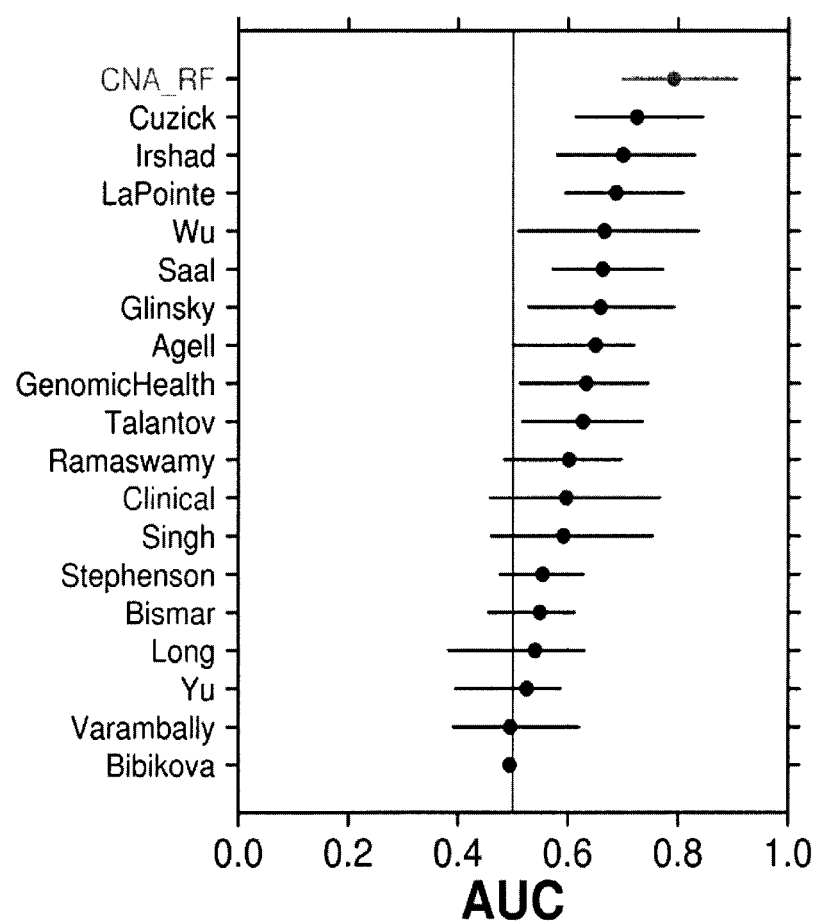
FIGS. 4C-D illustrate the improvement in the area under the curve (AUC) when using this signature on the low to intermediate risk MSKCC patients (C) and the low to high risk MSKCC patients (D) compared to previously published RNA signatures, or standard clinical variables.
Figure 4D:
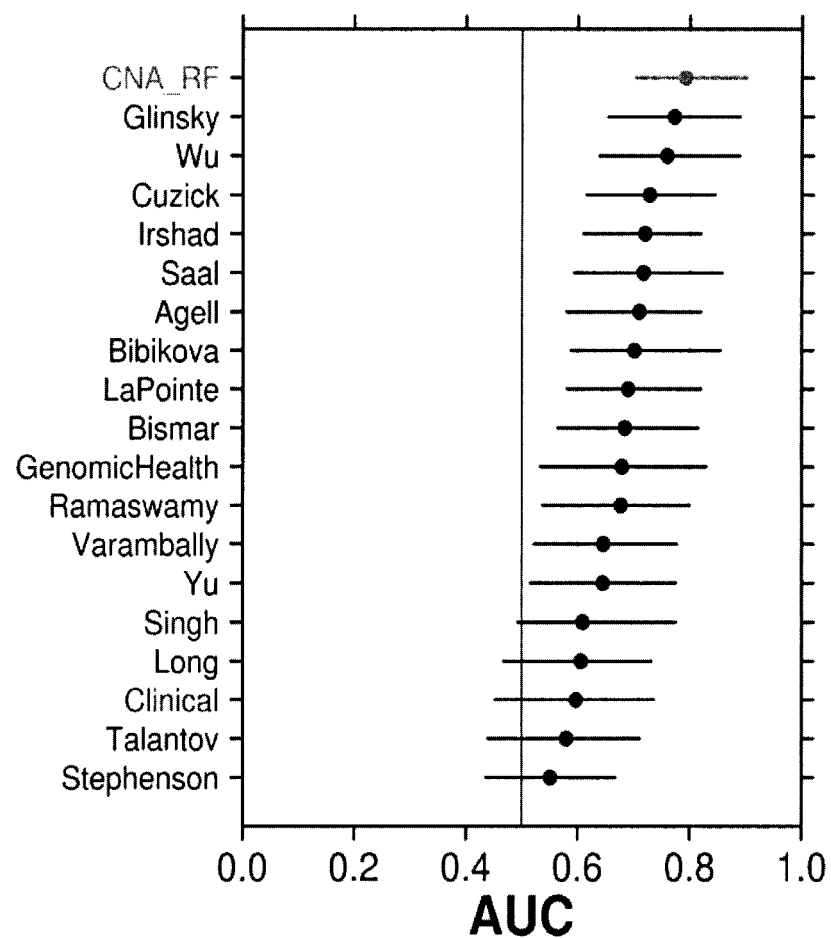

In addition to the genomic models, a clinical model was created using pre-treatment PSA, T category, and diagnostic Gleason score. Again a random forest model was used and tuned in a similar way as described above. The scores of the models were evaluated for their ability to predict biochemical relapse at 5 years and 18 months using survivalROC. Confidence intervals were estimated via 500 bootstrapping iterations. The AUCs for the 23 RNA signatures were compared to the AUC of our 100-loci DNA signature, using the 108 MSKCC patients with both mRNA and DNA information (FIG. 4C-D).

Example 1

Training and Validation Cohorts for a Biopsy-Based Signature of Prostate Cancer Aggression We used information derived from pre-IGRT biopsies (training/Toronto-IGRT cohort) and initially validated with public RadP specimens (validation/MSKCC cohort). A secondary independent cohort of 117 RadP specimens was obtained for further validation of putative biomarkers (validation/Cambridge cohort). The RadP cohorts were considered both separately and together ("Pooled RadP"). We focused on clinically-matched validation cohorts containing low- and intermediate-risk patients ("low+int", n=210) which might require treatment intensification beyond local therapy alone, but also considered all patients with localized disease (who might be candidates for intensification or de-intensification; "full" validation cohort, n=271). The biochemical relapse-free rates (bRFR) of the three cohorts were broadly comparable. Pre-treatment PSA was prognostic in IGRT patients, while pre-treatment GS, T-category, and PSA were all prognostic in the full MSKCC and Cambridge cohorts.

Four prognostic indices were developed and validated for prediction of BCR. First, unique genomic subtypes were identified using unsupervised hierarchical clustering. Second, the percentage of a patient's genome harbouring CNAs (percent genome alteration; PGA) was used as a surrogate for genomic instability, and evaluated together with tumour hypoxia. Finally, supervised machine learning with a random forest was used to identify a CNA signature, which was compared to published RNA-based signatures.

Example 2

Defining Four Genomic Subtypes of Localized Prostate Cancer

Our initial analyses showed that Toronto-IGRT and MSKCC cohorts showed extensive genomic heterogeneity, even for patients that were solely low- or intermediate-risk, or GS 6 or 7. The most recurrent CNAs in either cohort include 8p amplifications and 8q deletions, as well as deletions of 16q23•2 and 6q15 (harbouring MAF and MAP3K7), which have been observed in aggressive tumours, (Table 2). We then determined the frequency of CNAs (i.e. CNA recurrence) for a set of putative adverse prognostic genes, selected from our previous studies and the literature, in the Toronto-IGRT biopsies. Despite low- or intermediate-risk classification, 60% (76/126) of patients had CNAs in at least two adverse prognosis genes. This variability occurred across the genome (see PGA discussed below) and suggested that genomically-defined CaP subtypes might be obtained from biopsies.

Unbiased hierarchical clustering in the Toronto-IGRT cohort revealed four subtypes with distinct genomic profiles: Subtype-1 (characterized by gain of chromosome 7); Subtype-2 (deletion of 8p and gain of 8q); Subtype-3 (loss of 8p and 16q); and Subtype-4 ("quiet" genomes) (FIG. 1A, Tables 3, 4 and 5). Subtypes 2 and 3 share many common genetic alterations (504 genes altered in >25% of patients in both subtypes), yet chi-squared tests revealed eight regions which differed significantly, including gain of 8q (c-MYC has the smallest p-value) in Subtype-2 and 16q deletion in Subtype-3. All four subtypes were confirmed in the MSKCC RadP cohort and were not associated with TMPRSS2:ERG fusion, GS, or T-category.

In a pooled (Toronto-IGRT+MSKCC) low+int cohort analysis (n=250), the four genomic subtypes of localized CaP are associated with significantly different prognosis, even after adjustment for clinical variables (FIG. 1B). The 5-year bRFRs ranged from 53% (Subtype-3) to 89% (Subtype-4). Interestingly, Subtype-1 appears to be characterized by increased relapse after 3 years, rather than increased risk at all times. These subtypes are prognostic by 18 months (log-rank p=0•0024, low-int cohort), which is associated with increased PCSM. Indeed, in the Toronto-IGRT cohort, Subtype-2 is associated with overall survival (OS) (MVA $HR_{OS}$=4•2 (1•2–15), Wald p=0•03).

Example 3

Heterogeneity in Genomic Instability in Curable Prostate Cancers

Figure 2A:
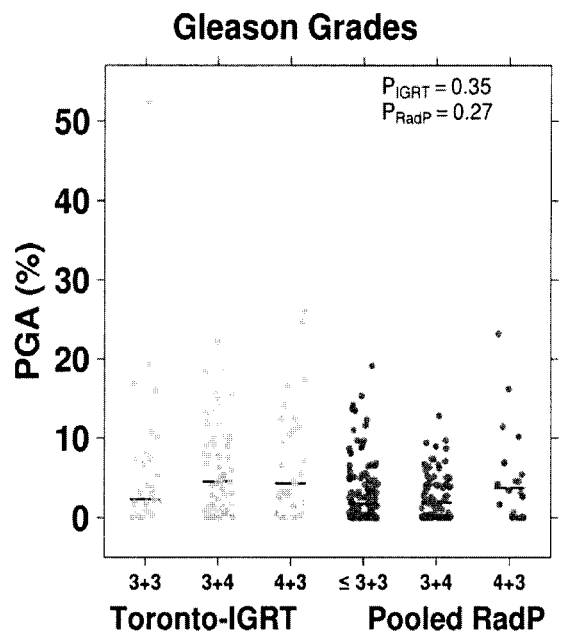
FIG. 2, which illustrates genomic instability as measured by PGA, demonstrating that PGA is prognostic independent of clinical factors. Specifically, it is shown that PGA is not a proxy for Gleason grades (FIG. 2A), pathological T group (FIG. 2B), or PSA (FIG. 2C) (Mann-Whitney U test).
FIG. 2D shows that Toronto-IGRT patients with PGA above the upper tertile PGA have statistically faster rates of biochemical recurrence.
In FIG. 2E-F, this same PGA threshold is prognostic in the pooled RadP cohort (MSKCC and Cambridge combined) of low- to intermediate-risk patients at 5-years (E) and of low- to high-risk patients at 18-months (F) after diagnosis.
Figure 2B:
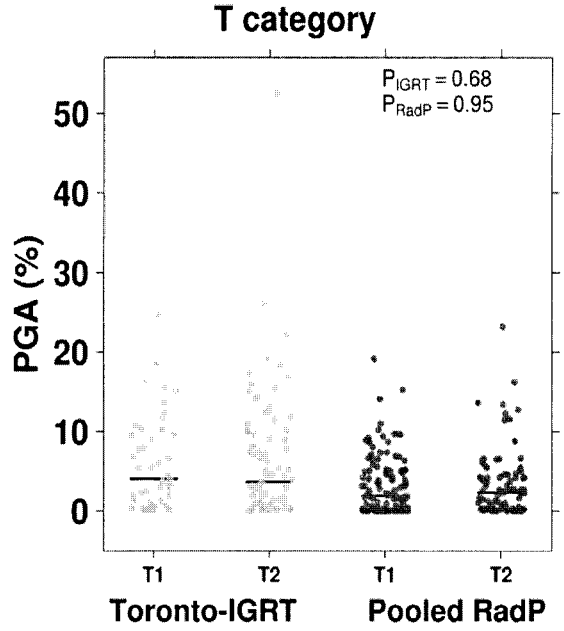
Figure 2C:
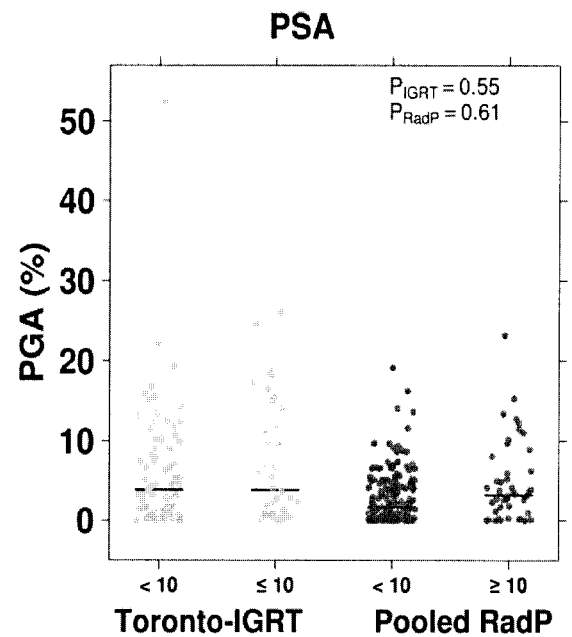

The excellent prognosis of "quiet" Subtype-4 suggested genome-wide instability might be prognostic in itself. Using the percentage of the genome showing a copy-number alteration (PGA) as a proxy for genomic instability, we observed inter-patient PGA variability ranging from 0-52% in the Toronto-IGRT cohort, 0-34% in the MSKCC cohort, and 0-28% in the Cambridge cohort. PGA was independent of GS, T-category, and PSA in all cohorts (FIGS. 2A-C). Indeed, individual GS 6 tumours showed higher PGA than some GS 4+3 tumours, suggesting PGA refines biological description even in predominant pattern 4 tumours. As expected, PGA was elevated in patients with prognostic CHD1 deletions (Baca et al., 2013).

Figure 2D:
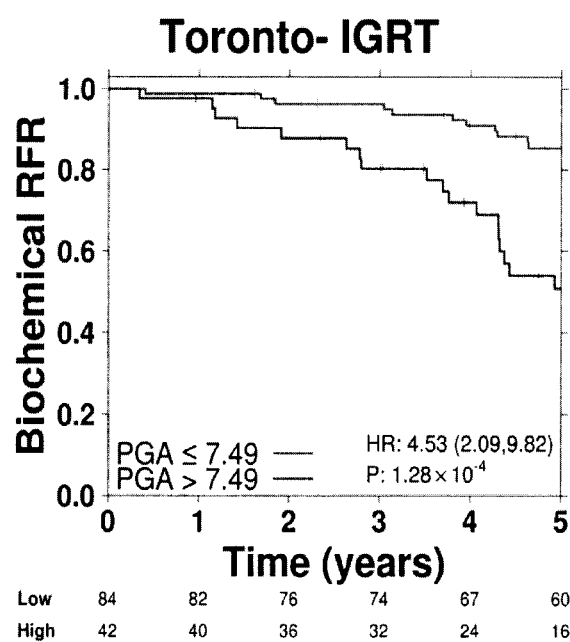
Figure 2E:
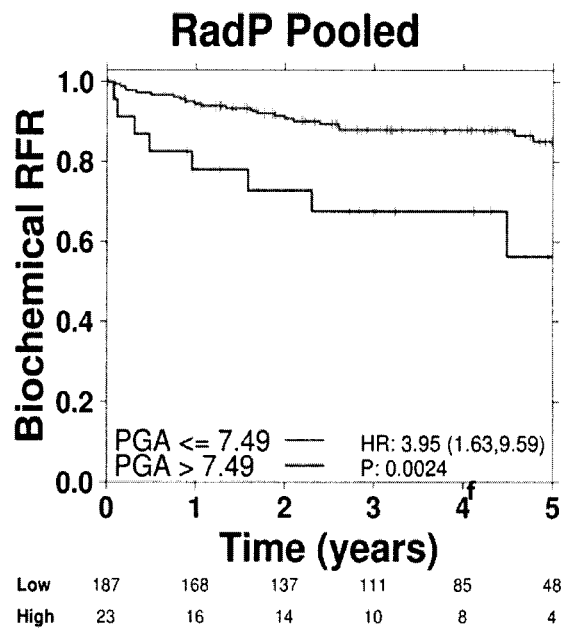
Figure 2F:
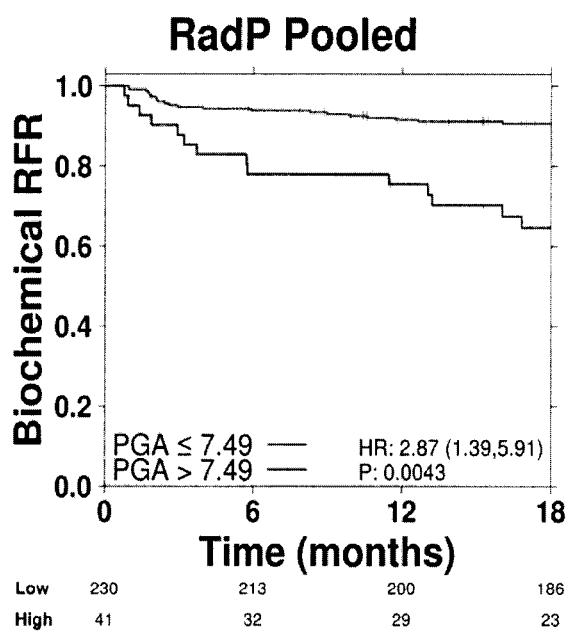

We noted that PGA itself was strongly prognostic, independent of clinical covariates, as recently reported. Remarkably, every 1% increase in PGA led to a 5-8% decrease in bRFR (C-index 0.60-0.72). To classify the likelihood of clinical failure based on PGA, we set the upper tertile of 7•49% from the Toronto-IGRT cohort as the lower bound threshold, which efficiently stratifies patients treated with either IGRT (MVA $HR_{BCR}$=4•5 (2•1-9•8), Wald p=0•00013) or RadP (e.g. pooled RadP low-int cohort MVA $HR_{BCR}$=4•0 (1•6-9•6), Wald p=0•0024; FIG. 2D-E). These results are threshold-independent. PGA stratifies patients at risk of rapid failure consistent with occult metastases, and indeed is elevated in the primary tumours of patients that developed metastases relative to those who did not and had a follow-up time of at least five years (median 9•2% (3•6-13) vs. 2•8% (0•33-6•8), p=0•0043 pooled Toronto-IGRT and MSKCC cohorts, two-sided Mann-Whitney U-test).

The median PGA differed significantly among our genomic subtypes, with Subtypes 1 and 4 having the highest (12% (8•9-16)) and lowest (1•3% (0•16-3•2)) median PGA. After the addition of PGA to the multivariate Cox proportional hazard model for subtypes, only Subtypes 2-3 remained prognostic, suggesting that their prognostic ability stems from both specific genetic aberrations and general genomic instability.

Example 4

Synergy Between Genomic Instability and Microenvironmental Indices of Failure

Figure 3A:
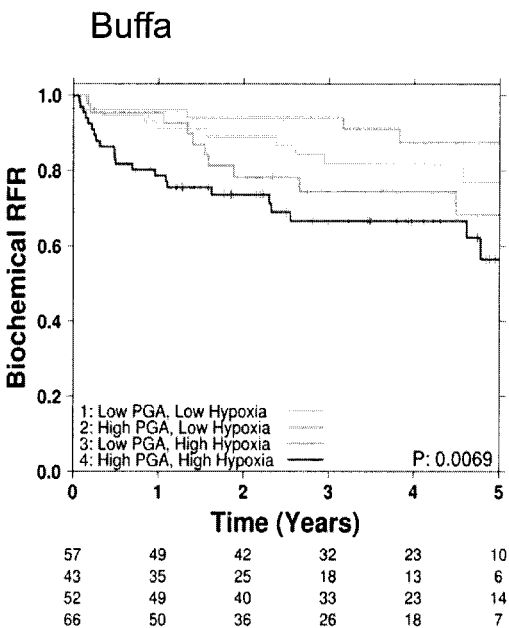
FIG. 3A-C illustrates the additive effect of hypoxia (as measured by three different RNA signatures (Buffa 2010; Eustace 2013; Winter 2007)) and PGA in the pooled RadP cohort (MSKCC and Cambridge combined).
Figure 3B:
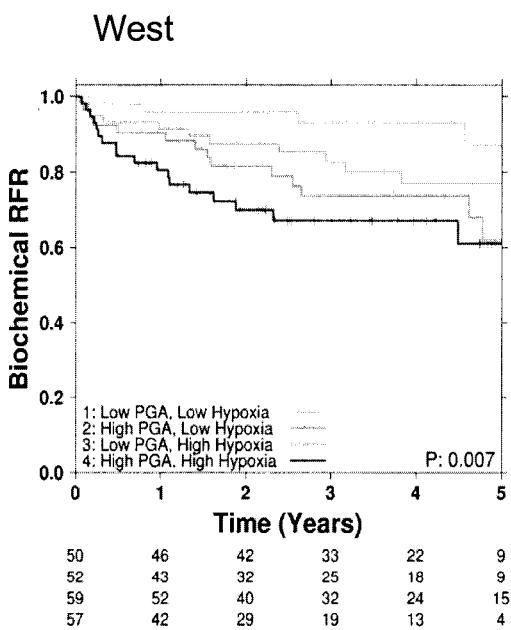
Figure 3C:
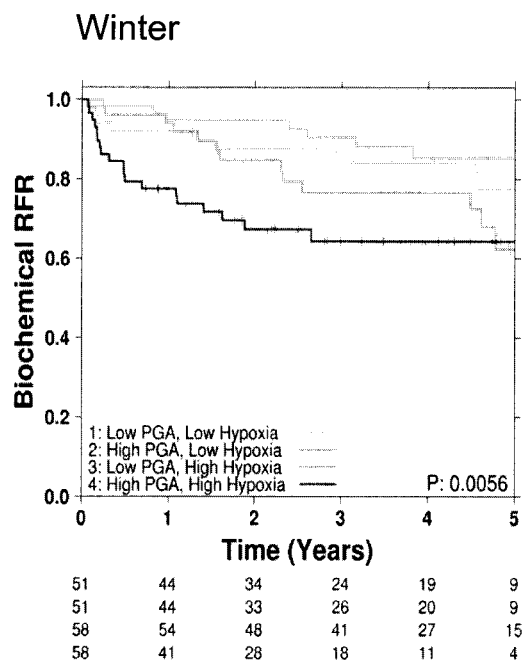

Hypoxia is an important aspect of cancer metabolism and in itself can be prognostic in CaP (Milosevic 2012; Vergis 2008). However, no study has simultaneously measured cancer-related genomic and tumour microenvironment indices to explore surrogacy versus synergy in stratifying patient outcome. As a first approach, we used three hypoxia RNA signatures that have been validated in other tumour types to estimate hypoxia within the pooled RadP mRNA cohorts (108 MSKCC patients and 110 Cambridge patients) (Buffa 2010; Eustace 2013; Winter 2007). This is, to our knowledge, the first attempt to apply these signatures to predict CaP outcome. None of these signatures were univariately prognostic, nor were they related to GS, PSA, T-category, or PGA. However when we separated patients into four groups based on high vs. low PGA and high vs. low hypoxia values, we observed a reproducible and unique effect of hypoxia being additive to PGA for prognosis. Patients with high PGA and high hypoxia have the worst prognosis, whereas patients with high hypoxia alone (low PGA) responded well following RadP (FIG. 3A-C).

Figure 3D:
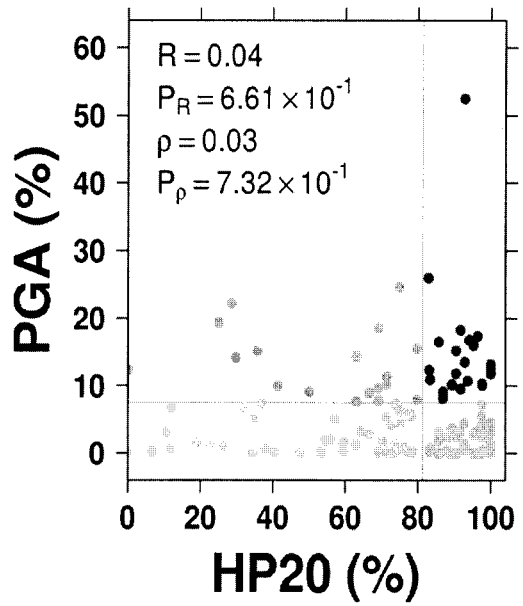
FIG. 3D shows there is no correlation between PGA and continuous HP20 or dichotomized HP20 in the Toronto-IGRT cohort (FIG. 3C).

To validate this provocative observation, we used the Toronto-IGRT cohort as the biobanking of frozen biopsies was completed with simultaneous and direct assessment of tumour hypoxia at the same intra-prostatic locale (Milosevic et al., 2012). This unique cohort therefore contained direct measurements of hypoxia denoted by patient-specific HP20 values (i.e. the percentage of oxygen measurements less than 20 mm Hg). The median HP20 in our cohort was 81% (64-93%), and trended to an association with elevated bRFR (log-rank p=0•13) consistent with the previous observation in a larger cohort that hypoxia was independently prognostic of IGRT outcome (Milosevic et al., 2012). Directly measured HP20 values were not related to the clinical covariates, genomic subtype, PGA (FIG. 3D), or with any individual CNA, supporting a unique role in prostate cancer tumour biology. We again found that patients with low PGA and low hypoxia had the best outcome (5-year bRFR=93%), while those with high PGA and high hypoxia had the worst (5-year bRFR=49%, FIG. 3E). Moreover, there was a statistically significant interaction between PGA and hypoxia (unadjusted $HR_{BCR}$=3•8 (1•7-8•7), Wald p=0•013) when used as a combined prognostic index. Again, patients whose tumour solely showed hypoxia, but not PGA, fared relatively well following IGRT, suggesting cohorts of patients with high hypoxia and high PGA could benefit from treatment intensification.

Example 5

A Novel Gene-Specific Prognostic Signature for Biochemical Relapse

Given that specific genes (FIG. 1), general genomic instability (FIG. 2), and tumour microenvironment (FIG. 3) all play a role in determining patient prognosis, we postulated that a supervised machine learning approach would capture the complex and unknown interactions between genes underlying these phenomena. Using a random forest (Breiman, 2001) classifier trained on the Toronto-IGRT cohort, we developed a biopsy-driven prognostic signature that predicts biochemical failure and could guide clinical decisions prior to, and independent of, treatment. The resulting 100-loci (276 genes; Table 1) DNA signature was validated in two independent cohorts (FIG. 4A-B). It was first verified in the independent low+int MSKCC cohort, where it predicted BCR with an AUC of 0•74. This is superior to clinical variables (p=0•01 vs. NCCN). MSKCC patients classified as poor-prognosis have 5-year bRFR of 58% compared to 89% for those classified as good-prognosis, and this difference remains significant after adjustment for clinical covariates (MVA $HR_{BCR}$=6•1 (2•0-19), Wald p=0•0015). Importantly, our signature effectively identified patients at risk of relapse within 18-months in the full MSKCC cohort, despite not including any high-risk patients in the initial training cohort (MVA $HR_{BCR}$=3•3, (1•1-10), Wald p=0•038). This early-failure effect was validated in a second independent Cambridge cohort (MVA $HR_{BCR}$=2.8, (1•7-9•4), Wald p=0•050). The signature is independent of clinical covariates and indeed shows promise in identifying candidates for both treatment intensification and de-intensification protocols as it can identify GS 7 patients that will fail within 18 months ($HR_{BCR}$=2•8 (1•2-6•7), p=0•021) and was also highly prognostic for low-risk patients (AUC=0•97). Importantly, the signature identified patients that go on to develop metastasis (AUC=0•78).

To underpin the potential use of our DNA signature, we observed that it exceeded 97% (970,000/1,000,000) of the empirical null distribution from randomly sampled genesets. Our signature also outperformed 23 previously published RNA signatures for CaP-associated bRFR after training random forests with a cohort of 1299 low to high risk prostate cancer patients with mRNA microarray data, including 293 low to intermediate risk patients. Applying these trained forests to the 108 MSKCC patients with both mRNA and CNA information, revealed that our DNA-signature has the highest overall AUC (FIG. 4C-D).

Most genes in the signature are altered at relatively low rates, with 56% (154/276) altered in fewer than 10% (39/397) of patients. These results strongly support the use of multi-gene models, as our biopsy-based DNA-signature outperformed reported prognostic genes. Signature regions are distributed across 14 chromosomes, and range by an order-of-magnitude in their importance to prediction-accuracy. Interestingly, genes in these regions relate to lipid metabolism.

We also found that the signature directly accounts for genomic instability. First, patients with Subtype-4 tumours have significantly lower Signature Risk Scores than the other subtypes (0•17 (0•0026-0•32) vs. 0.41 (0•31-0•61), p<0•0001, two-sided Mann-Whitney U-test). Secondly, PGA differs significantly between the classes predicted by the signature and can be estimated from the gene signature (Spearman's correlation between whole-genome and signature-estimated PGA p=0•73; p<0.0001), thereby providing similar prognostic information. Importantly, signature-based estimates of PGA remain highly prognostic, and adding 30 genes (selected from the Toronto-IGRT cohort) improves PGA estimates in the validation cohorts (e.g. MSKCC: Spearman's p=0•73 vs. 0.87; p<0•0001). The HR of continuous PGA estimated from these 306 genes is identical to that of true PGA in the MSKCC cohort and nearly identical for the Cambridge cohort. Taken together, these results indicate that our treatment-independent, DNA prognostic signature measures genomic instability in addition to lipid metabolism pathways.

Results

Development of CaP biomarkers to guide disease management at the time of diagnosis is a difficult yet critical ongoing challenge, given the high rates of over-treatment and clinical relapse (Presner 2012). Here we developed clinically-relevant prognostic indices using integrated tumour DNA and microenvironmental indices (prognostic indices are summarized in Table 6). Initial investigation in the Toronto-IGRT cohort consisting of 126 low- to intermediate-risk patients revealed striking genomic heterogeneity in the pre-treatment biopsies from these patients, and has implications for the discovery of driver mutations in CaP. No CNAs were recurrent in more than 47% of patients and the number of CNAs per patient ranged from 0 to 187. We were, however, able to identify independent molecular prognostic subtypes based on genome-wide CNA profiles in the Toronto-IGRT cohort. Including additional patients from the independent MSKCC cohort of low- and intermediate-risk CaP patients led to larger subtype sizes amenable to bRFR analyses, revealing statistically significant differences in patient outcome according to subtype. Our CNA-based signature (100 regions across 14 chromosomes), identifies patients which differ 6-times in bRFR, and patients at risk of failure within 18 months, all within the current clinical context of GS, T-category, and PSA. In particular, this signature is highly effective for low-risk patients, identifying those ineligible for active surveillance and providing additional assurance for those who are. For instance, if the DNA signature was used in clinic today, of 1000 patients diagnosed with localized disease, 144 patients would be offered more aggressive treatment (all signature-positive patients), and 650 would have the support for active surveillance instead of local treatment (low-int signature-negative patients).

Pre-clinical experimental work supports hypoxia generating a mutator phenotype and selecting for genetically unstable clones, along with an increased capacity for distant metastases (Bristow 2008). This metastatic phenotype is independent of local treatment and indeed hypoxia is a poor prognostic marker regardless of treatment modality; it is associated with both local relapse after IGRT and also biochemical failure and distant metastasis in patients receiving IGRT or RadP for prostate cancer (Milosevic 2012; Vergis 2008). Now, we have also shown that simultaneous measurement of tumour hypoxia and genomic instability can improve the prognostic capability of a pre-treatment biopsy by marrying the independent biology of cancer genomics and the tumour microenvironment. It also suggests that the poor prognosis previously associated with hypoxia (e.g. Milosevic 2012 and Vergis 2008) may have been related to genomic instability within a subset of these specimens, given that hypoxia itself was not associated with poor prognosis in the absence of heightened PGA.

Cancer cell metabolism (increased glycolysis, high lactate, and hypoxia) is related to oncogene activation and tumor suppressor loss, and increased lipid and fatty acid synthesis have been associated with CaP progression (Fritz 2013; Yue 2014). It is intriguing that our supervised machine learning approach led to a signature enriched for genes involved in lipid biology. Combined with the finding that constitutive activation of mTORC1 renders hypoxic cells dependent on exogenous desaturated lipids, our signature could represent abnormalities in cancer metabolism amenable to targeting of lipid synthesis (Fritz 2013; Menon 2008; Young 2013; Yue 2014). In addition, our signature efficiently captures the prognostic impact of PGA, a surrogate for genomic instability. Given that ADT has been shown to both improve oxygenation (Milosevic 2007) and reduce DNA repair (Goodwin 2013) in CaP, we speculate that such therapies targeting hypoxia and genomic instability may be effective in preventing clinical relapse. Patients flagged by our signature may benefit from patient-specific intensification with ADT or other systemic therapies to offset both local and systemic resistance, independent of primary treatment.

To our knowledge, this is the first report of biopsy-driven, DNA-based indices that predict prognosis in patients who received either IGRT or RadP as primary therapy for CaP. Compared to RNA abundance, DNA alterations may be less variable within intra-prostatic biopsies from dynamic tumour microenvironments, and more stable ex vivo during FFPE protocols. This suggests that our DNA signatures are robust for clinical application. As our training cohort was obtained prior to primary therapy, our study supports the characterization of complex indices reflecting inter-patient heterogeneity a priori, soon after diagnostic MRI- or trans-urethral ultrasound-guided biopsies. Indeed, we have recently shown that frozen biopsies are amenable to whole genome sequencing to evaluate intra-patient heterogeneity in genomic aberrations (unpublished data; Boutros et al.).

There are several caveats to this study. Using BCR as an end-point is sub-optimal compared to PSCM or time to metastasis. Nonetheless, our signature shows promise in discriminating patients with metastasis, and can identify patients that will experience BCR prior to 18 months, which is predictive for PCSM (Buyyounouski 2012; Freedland 2005). Although the cohorts differ slightly in the distribution of clinico-pathologic factors, these differences neither altered treatment nor survival, making it very unlikely that this affects the interpretation of our results. Nevertheless, we do systematically stratify our analyses according to these factors when assessing prognostic markers. A subset of patients were treated with adjuvant treatment, however at this time we do not know how adjuvant treatment affects our signature performance.

From a technical perspective, despite different resolutions between the CNA platforms used for each cohort, the CNA indices developed in the Toronto-IGRT cohort validated in the RadP cohorts. The hypoxia probes measure global hypoxia within a prostate cancer locale, but do not measure intracellular hypoxia. As a result, the DNA is obtained from a large region relative to sites of hypoxia. In future studies we will characterize the DNA, RNA, and epigenetic profiles of foci within patients that orally receive pimonidazole prior to treatment to investigate the genomic-hypoxia prognostic relationship in finer detail. Finally, efforts are underway to reduce the signature size without losing prognostic information related to metabolism or genomic instability, and to improve the sensitivity of our signature with multimodal data sets (e.g. combined DNA, RNA and epigenetic analyses) emerging from TCGA and ICGC studies.

Identifying the correct patients to treat while avoiding over-treatment in the low- to intermediate-risk group remains an important clinical dilemma. We envision the use of genomic instability-microenvironment signatures to divert patients from current clinical risk categories into novel clinical trials of treatment intensification whereby patients with poor prognosis based on these novel biomarkers can be culled into trials which add combined local and systemic therapies. Additionally, low and intermediate risk patients that have low levels of hypoxia and PGA could be entered into clinical trials of active surveillance. These precision medicine approaches set the stage for novel treatment intensification and treatment de-intensification trials to either increase cure rates by preventing progression to mCRPC or to reduce the burden of overtreatment.

The embodiments of the present disclosure described above are intended to be examples only. Alterations, modifications and variations to the disclosure may be made without departing from the intended scope of the present disclosure. In particular, selected features from one or more of the above-described embodiments may be combined to create alternative embodiments not explicitly described. All values and sub-ranges within disclosed ranges are also disclosed. The subject matter described herein intends to cover and embrace all suitable changes in technology. All references mentioned are hereby incorporated by reference in their entirety.

TABLE 1

Locus Rankings. Locus regions within a human prostate tumour genome, the genes contained within each respective locus, the chromosome associated with each gene as well as the start and end nucleotide number associated with each gene on each respective chromosome is shown. Gene regions are based on the hg19 human genome reference (NCBI GRCh37 Genome Reference Consortium Human Reference 37). Each locus, comprised of one or a plurality of genes, is ranked from 1 to 100, based on the Gini Score from the random forest model. Locus rank refers to the order in which they were added to the model.

| Rank | Locus | Locus Start | Locus End | Symbol | EntrezID | Chromosome | Gene Start | Gene End |
|---|---|---|---|---|---|---|---|---|
| 1 | 1 | 21549529 | 21646346 | GFRA2 | 2675 | 8 | 21549529 | 21646346 |
| 2 | 41 | 40962149 | 41065386 | AOC2 | 314 | 17 | 40996608 | 41002724 |
| 2 | 41 | 40962149 | 41065386 | AOC3 | 8639 | 17 | 41003200 | 41010140 |
| 2 | 41 | 40962149 | 41065386 | BECN1 | 8678 | 17 | 40962149 | 40976310 |
| 2 | 41 | 40962149 | 41065386 | G6PC | 2538 | 17 | 41052814 | 41065386 |
| 2 | 41 | 40962149 | 41065386 | PSME3 | 10197 | 17 | 40985422 | 40995777 |
| 3 | 2 | 8559665 | 8890849 | CLDN23 | 137075 | 8 | 8559665 | 8561617 |
| 3 | 2 | 8559665 | 8890849 | ERI1 | 90459 | 8 | 8860313 | 8890849 |
| 3 | 2 | 8559665 | 8890849 | MFHAS1 | 9258 | 8 | 8641998 | 8751131 |
| 4 | 21 | 113139327 | 113242481 | TUBGCP3 | 10426 | 13 | 113139327 | 113242481 |
| 5 | 33 | 131265453 | 131978646 | EBF3 | 253738 | 10 | 131633495 | 131762091 |
| 5 | 33 | 131265453 | 131978646 | GLRX3 | 10539 | 10 | 131934638 | 131978646 |
| 5 | 33 | 131265453 | 131978646 | MGMT | 4255 | 10 | 131265453 | 131565783 |
| 6 | 99 | 136469715 | 136659848 | KHDRBS3 | 10656 | 8 | 136469715 | 136659848 |
| 7 | 98 | 135490030 | 135725292 | ZFAT | 57623 | 8 | 135490030 | 135725292 |
| 8 | 79 | 83637442 | 84746935 | NRG3 | 10718 | 10 | 83637442 | 84746935 |
| 9 | 4 | 90640025 | 90775542 | ACTA2 | 59 | 10 | 90694830 | 90751147 |
| 9 | 4 | 90640025 | 90775542 | FAS | 355 | 10 | 90750287 | 90775542 |
| 9 | 4 | 90640025 | 90775542 | STAMBPL1 | 57559 | 10 | 90640025 | 90683244 |
| 10 | 3 | 90579658 | 90611732 | ANKRD22 | 118932 | 10 | 90579658 | 90611732 |
| 11 | 15 | 8175257 | 8239257 | PRAGMIN | 157285 | 8 | 8175257 | 8239257 |
| 12 | 16 | 7305275 | 7754237 | DEFB104A | 140596 | 8 | 7327829 | 7698764 |
| 12 | 16 | 7305275 | 7754237 | DEFB104B | 503618 | 8 | 7327829 | 7698764 |
| 12 | 16 | 7305275 | 7754237 | DEFB105A | 245908 | 8 | 7345242 | 7681360 |
| 12 | 16 | 7305275 | 7754237 | DEFB105B | 504180 | 8 | 7345242 | 7681360 |
| 12 | 16 | 7305275 | 7754237 | DEFB106A | 245909 | 8 | 7340025 | 7686575 |
| 12 | 16 | 7305275 | 7754237 | DEFB106B | 503841 | 8 | 7340025 | 7686575 |
| 12 | 16 | 7305275 | 7754237 | DEFB107A | 245910 | 8 | 7353367 | 7673238 |
| 12 | 16 | 7305275 | 7754237 | DEFB107B | 503614 | 8 | 7353367 | 7673238 |
| 12 | 16 | 7305275 | 7754237 | DEFB4 | 1673 | 8 | 7752198 | 7754237 |
| 12 | 16 | 7305275 | 7754237 | SPAG11A | 653423 | 8 | 7705401 | 7721319 |
| 12 | 16 | 7305275 | 7754237 | SPAG11B | 10407 | 8 | 7305275 | 7321192 |
| 13 | 12 | 8993763 | 9009152 | PPP1R3B | 79660 | 8 | 8993763 | 9009152 |
| 14 | 58 | 43511808 | 43586893 | PSG11 | 5680 | 19 | 43511808 | 43530631 |
| 14 | 58 | 43511808 | 43586893 | PSG2 | 5670 | 19 | 43568361 | 43586893 |
| 15 | 40 | 7286415 | 7740105 | DEFB103A | 55894 | 8 | 7286415 | 7740180 |
| 15 | 40 | 7286415 | 7740105 | DEFB103B | 414325 | 8 | 7286490 | 7740105 |
| 16 | 37 | 191625 | 256814 | ATP11A | 23250 | 13 | 113344642 | 113541482 |
| 16 | 37 | 191625 | 256814 | C13orf35 | 400165 | 13 | 113301357 | 113338811 |
| 16 | 37 | 113301357 | 113754053 | MCF2L | 23263 | 13 | 113656027 | 113754053 |
| 17 | 6 | 48972117 | 49147744 | FAM19A5 | 25817 | 22 | 48972117 | 49147744 |
| 18 | 43 | 149570056 | 149577787 | ATP6V0E2 | 155066 | 7 | 149570056 | 149577787 |
| 19 | 42 | 149535508 | 149564568 | ZNF862 | 643641 | 7 | 149535508 | 149564568 |
| 20 | 11 | 47158517 | 47571342 | TBC1D22A | 25771 | 22 | 47158517 | 47571342 |
| 21 | 39 | 149473130 | 149531053 | SSPO | 23145 | 7 | 149473130 | 149531053 |
| 22 | 22 | 12869772 | 12887284 | C8orf79 | 57604 | 8 | 12869772 | 12887284 |

TABLE 1-continued

Locus Rankings. Locus regions within a human prostate tumour genome, the genes contained within each respective locus, the chromosome associated with each gene as well as the start and end nucleotide number associated with each gene on each respective chromosome is shown. Gene regions are based on the hg19 human genome reference (NCBI GRCh37 Genome Reference Consortium Human Reference 37). Each locus, comprised of one or a plurality of genes, is ranked from 1 to 100, based on the Gini Score from the random forest model. Locus rank refers to the order in which they were added to the model.

| Rank | Locus | Locus Start | Locus End | Symbol | EntrezID | Chromosome | Gene Start | Gene End |
|---|---|---|---|---|---|---|---|---|
| 23 | 23 | 12579405 | 12612992 | LONRF1 | 91694 | 8 | 12579405 | 12612992 |
| 24 | 97 | 88744089 | 88781786 | C16orf84 | 348180 | 16 | 88772890 | 88781786 |
| 24 | 97 | 88744089 | 88781786 | RNF166 | 115992 | 16 | 88762902 | 88772829 |
| 24 | 97 | 88744089 | 88781786 | SNAI3 | 333929 | 16 | 88744089 | 88752882 |
| 25 | 95 | 88003623 | 88601574 | BANP | 54971 | 16 | 88003623 | 88110924 |
| 25 | 95 | 88003623 | 88601574 | ZFPM1 | 161882 | 16 | 88520013 | 88601574 |
| 26 | 5 | 90033620 | 90343082 | RNLS | 55328 | 10 | 90033620 | 90343082 |
| 27 | 96 | 88636788 | 88729495 | CYBA | 1535 | 16 | 88709696 | 88717492 |
| 27 | 96 | 88636788 | 88729495 | IL17C | 27189 | 16 | 88705000 | 88706882 |
| 27 | 96 | 88636788 | 88729495 | MVD | 4597 | 16 | 88718347 | 88729495 |
| 27 | 96 | 88636788 | 88729495 | ZC3H18 | 124245 | 16 | 88636788 | 88698372 |
| 28 | 29 | 9413444 | 9639856 | TNKS | 8658 | 8 | 9413444 | 9639856 |
| 29 | 38 | 72937384 | 73024522 | GLT8D4 | 727936 | 3 | 72937384 | 73024522 |
| 30 | 78 | 87863628 | 87970112 | CA5A | 763 | 16 | 87921624 | 87970112 |
| 30 | 78 | 87863628 | 87970112 | SLC7A5 | 8140 | 16 | 87863628 | 87903100 |
| 31 | 32 | 111530886 | 111567416 | ANKRD10 | 55608 | 13 | 111530886 | 111567416 |
| 32 | 44 | 42607779 | 42623929 | CHRNA6 | 8973 | 8 | 42607779 | 42623929 |
| 33 | 56 | 11141999 | 11189695 | AMAC1L2 | 83650 | 8 | 11188494 | 11189695 |
| 33 | 56 | 11141999 | 11189695 | MTMR9 | 66036 | 8 | 11141999 | 11185654 |
| 34 | 25 | 90965693 | 90967071 | CH25H | 9023 | 10 | 90965693 | 90967071 |
| 35 | 24 | 90346518 | 90537999 | LIPF | 8513 | 10 | 90424145 | 90438572 |
| 35 | 24 | 90346518 | 90537999 | LIPJ | 142910 | 10 | 90346518 | 90366733 |
| 35 | 24 | 90346518 | 90537999 | LIPK | 643414 | 10 | 90484300 | 90512513 |
| 35 | 24 | 90346518 | 90537999 | LIPN | 643418 | 10 | 90521162 | 90537999 |
| 36 | 63 | 116638561 | 117072975 | AMBP | 259 | 9 | 116822407 | 116840752 |
| 36 | 63 | 116638561 | 117072975 | COL27A1 | 85301 | 9 | 116918230 | 117072975 |
| 36 | 63 | 116638561 | 117072975 | KIF12 | 113220 | 9 | 116853917 | 116861337 |
| 36 | 63 | 116638561 | 117072975 | ZNF618 | 114991 | 9 | 116638561 | 116818875 |
| 37 | 51 | 42396938 | 42408140 | C8orf40 | 114926 | 8 | 42396938 | 42408140 |
| 38 | 76 | 11994676 | 12051624 | DUB3 | 377630 | 8 | 11994676 | 11996269 |
| 38 | 76 | 11994676 | 12051624 | FAM86B1 | 85002 | 8 | 12039612 | 12051624 |
| 39 | 75 | 11921897 | 11973025 | DEFB130 | 245940 | 8 | 11921897 | 12175825 |
| 39 | 75 | 11921897 | 11973025 | ZNF705D | 728957 | 8 | 11946804 | 11973025 |
| 40 | 7 | 1201709 | 1295162 | SLC6A18 | 348932 | 5 | 1225469 | 1246304 |
| 40 | 7 | 1201709 | 1295162 | SLC6A19 | 340024 | 5 | 1201709 | 1225230 |
| 40 | 7 | 1201709 | 1295162 | TERT | 7015 | 5 | 1253286 | 1295162 |
| 41 | 8 | 1317999 | 1345002 | CLPTM1L | 81037 | 5 | 1317999 | 1345002 |
| 42 | 9 | 1392904 | 1445543 | SLC6A3 | 6531 | 5 | 1392904 | 1445543 |
| 43 | 30 | 60697516 | 60777810 | GTPBP5 | 26164 | 20 | 60758080 | 60777810 |
| 43 | 30 | 60697516 | 60777810 | LSM14B | 149986 | 20 | 60697516 | 60710434 |
| 43 | 30 | 60697516 | 60777810 | PSMA7 | 5688 | 20 | 60711790 | 60718474 |
| 43 | 30 | 60697516 | 60777810 | SS18L1 | 26039 | 20 | 60718821 | 60757566 |
| 44 | 54 | 42010463 | 42065194 | AP3M2 | 10947 | 8 | 42010463 | 42028701 |
| 44 | 54 | 42010463 | 42065194 | PLAT | 5327 | 8 | 42032235 | 42065194 |
| 45 | 53 | 42249278 | 42397068 | SLC20A2 | 6575 | 8 | 42273992 | 42397068 |
| 45 | 53 | 42249278 | 42397068 | VDAC3 | 7419 | 8 | 42249278 | 42263455 |
| 46 | 52 | 42195972 | 42234674 | DKK4 | 27121 | 8 | 42231585 | 42234674 |
| 46 | 52 | 42195972 | 42234674 | POLB | 5423 | 8 | 42195972 | 42229331 |
| 47 | 10 | 1009167 | 1112172 | NKD2 | 85409 | 5 | 1009167 | 1038925 |
| 47 | 10 | 1009167 | 1112172 | SLC12A7 | 10723 | 5 | 1050488 | 1112172 |
| 48 | 18 | 443333 | 467409 | EXOC3 | 11336 | 5 | 443333 | 467409 |
| 49 | 27 | 50166936 | 50218452 | BRD1 | 23774 | 22 | 50166936 | 50218452 |
| 50 | 91 | 56725982 | 57290900 | APCDD1L | 164284 | 20 | 57034425 | 57089949 |
| 50 | 91 | 56725982 | 57290900 | C20orf85 | 128602 | 20 | 56725982 | 56736183 |
| 50 | 91 | 56725982 | 57290900 | NPEPL1 | 79716 | 20 | 57267861 | 57290900 |
| 50 | 91 | 56725982 | 57290900 | RAB22A | 57403 | 20 | 56884770 | 56942563 |
| 50 | 91 | 56725982 | 57290900 | STX16 | 8675 | 20 | 57226308 | 57254582 |
| 50 | 91 | 56725982 | 57290900 | VAPB | 9217 | 20 | 56964174 | 57026156 |
| 51 | 55 | 135170364 | 135290723 | FBXL21 | 26223 | 5 | 135266005 | 135277367 |
| 51 | 55 | 135170364 | 135290723 | IL9 | 3578 | 5 | 135227934 | 135231516 |
| 51 | 55 | 135170364 | 135290723 | LECT2 | 3950 | 5 | 135282599 | 135290723 |
| 51 | 55 | 135170364 | 135290723 | LOC153328 | 153328 | 5 | 135170364 | 135224326 |
| 52 | 34 | 11700033 | 11853760 | CTSB | 1508 | 8 | 11700033 | 11725646 |
| 52 | 34 | 11700033 | 11853760 | DEFB134 | 613211 | 8 | 11851488 | 11853760 |
| 52 | 34 | 11700033 | 11853760 | DEFB136 | 613209 | 8 | 11839829 | 11842099 |
| 52 | 34 | 11700033 | 11853760 | DEFB137 | 613210 | 8 | 11831445 | 11832108 |
| 53 | 17 | 271735 | 443258 | AHRR | 57491 | 5 | 304290 | 438405 |
| 53 | 17 | 271735 | 443258 | C5orf55 | 116349 | 5 | 441642 | 443258 |
| 53 | 17 | 271735 | 443258 | PDCD6 | 10016 | 5 | 271735 | 315089 |
| 54 | 62 | 11561716 | 11696818 | FDFT1 | 2222 | 8 | 11660189 | 11696818 |
| 54 | 62 | 11561716 | 11696818 | GATA4 | 2626 | 8 | 11561716 | 11617509 |

TABLE 1-continued

Locus Rankings. Locus regions within a human prostate tumour genome, the genes contained within each respective locus, the chromosome associated with each gene as well as the start and end nucleotide number associated with each gene on each respective chromosome is shown. Gene regions are based on the hg19 human genome reference (NCBI GRCh37 Genome Reference Consortium Human Reference 37). Each locus, comprised of one or a plurality of genes, is ranked from 1 to 100, based on the Gini Score from the random forest model. Locus rank refers to the order in which they were added to the model.

| Rank | Locus | Locus Start | Locus End | Symbol | EntrezID | Chromosome | Gene Start | Gene End |
|---|---|---|---|---|---|---|---|---|
| 54 | 62 | 11561716 | 11696818 | NEIL2 | 252969 | 8 | 11627171 | 11644854 |
| 55 | 94 | 57466425 | 57617901 | ATP5E | 514 | 20 | 57603732 | 57607422 |
| 55 | 94 | 57466425 | 57617901 | CTSZ | 1522 | 20 | 57570241 | 57582309 |
| 55 | 94 | 57466425 | 57617901 | GNAS | 2778 | 20 | 57466425 | 57486250 |
| 55 | 94 | 57466425 | 57617901 | SLMO2 | 51012 | 20 | 57608199 | 57617901 |
| 55 | 94 | 57466425 | 57617901 | TH1L | 51497 | 20 | 57556310 | 57570188 |
| 55 | 94 | 57466425 | 57617901 | TUBB1 | 81027 | 20 | 57594308 | 57601709 |
| 56 | 20 | 612404 | 693510 | CEP72 | 55722 | 5 | 612404 | 653666 |
| 56 | 20 | 612404 | 693510 | TPPP | 11076 | 5 | 659976 | 693510 |
| 57 | 19 | 473333 | 524549 | SLC9A3 | 6550 | 5 | 473333 | 524549 |
| 58 | 13 | 795719 | 892939 | BRD9 | 65980 | 5 | 863849 | 892939 |
| 58 | 13 | 795719 | 892939 | ZDHHC11 | 79844 | 5 | 795719 | 851101 |
| 59 | 14 | 892968 | 918164 | TRIP13 | 9319 | 5 | 892968 | 918164 |
| 60 | 57 | 113845796 | 114466484 | C11orf71 | 54494 | 11 | 114262169 | 114271139 |
| 60 | 57 | 113845796 | 114466484 | FAM55A | 120400 | 11 | 114392436 | 114430580 |
| 60 | 57 | 113845796 | 114466484 | FAM55D | 54827 | 11 | 114441312 | 114466484 |
| 60 | 57 | 113845796 | 114466484 | HTR3A | 3359 | 11 | 113845796 | 113861034 |
| 60 | 57 | 113845796 | 114466484 | NNMT | 4837 | 11 | 114166534 | 114183238 |
| 60 | 57 | 113845796 | 114466484 | RBM7 | 10179 | 11 | 114271383 | 114279635 |
| 60 | 57 | 113845796 | 114466484 | REXO2 | 25996 | 11 | 114310107 | 114321000 |
| 60 | 57 | 113845796 | 114466484 | ZBTB16 | 7704 | 11 | 113930430 | 114121397 |
| 61 | 77 | 60549853 | 60640866 | TAF4 | 6874 | 20 | 60549853 | 60640866 |
| 62 | 26 | 50247496 | 50283726 | ZBED4 | 9889 | 22 | 50247496 | 50283726 |
| 63 | 47 | 7942357 | 7952451 | ALOX15B | 247 | 17 | 7942357 | 7952451 |
| 64 | 46 | 7905987 | 7923658 | GUCY2D | 3000 | 17 | 7905987 | 7923658 |
| 65 | 49 | 7999217 | 8151413 | ALOXE3 | 59344 | 17 | 7999217 | 8021860 |
| 65 | 49 | 7999217 | 8151413 | AURKB | 9212 | 17 | 8108048 | 8113883 |
| 65 | 49 | 7999217 | 8151413 | C17orf59 | 54785 | 17 | 8091650 | 8093564 |
| 65 | 49 | 7999217 | 8151413 | C17orf68 | 80169 | 17 | 8128138 | 8151413 |
| 65 | 49 | 7999217 | 8151413 | HES7 | 84667 | 17 | 8023907 | 8027410 |
| 65 | 49 | 7999217 | 8151413 | PER1 | 5187 | 17 | 8043787 | 8055753 |
| 65 | 49 | 7999217 | 8151413 | TMEM107 | 84314 | 17 | 8076296 | 8079714 |
| 65 | 49 | 7999217 | 8151413 | VAMP2 | 6844 | 17 | 8062464 | 8066293 |
| 66 | 45 | 7623038 | 7853237 | CHD3 | 1107 | 17 | 7792168 | 7816075 |
| 66 | 45 | 7623038 | 7853237 | CNTROB | 116840 | 17 | 7835441 | 7853237 |
| 66 | 45 | 7623038 | 7853237 | CYB5D1 | 124637 | 17 | 7761063 | 7765600 |
| 66 | 45 | 7623038 | 7853237 | DNAH2 | 146754 | 17 | 7623038 | 7737058 |
| 66 | 45 | 7623038 | 7853237 | KCNAB3 | 9196 | 17 | 7826026 | 7832753 |
| 66 | 45 | 7623038 | 7853237 | KDM6B | 23135 | 17 | 7743234 | 7758118 |
| 66 | 45 | 7623038 | 7853237 | LSMD1 | 84316 | 17 | 7760002 | 7761172 |
| 66 | 45 | 7623038 | 7853237 | TMEM88 | 92162 | 17 | 7758383 | 7759417 |
| 66 | 45 | 7623038 | 7853237 | TRAPPC1 | 58485 | 17 | 7833662 | 7835267 |
| 67 | 73 | 1568824 | 1599179 | NCRNA00168 | 642394 | 10 | 1568824 | 1599179 |
| 68 | 48 | 7975953 | 7991021 | ALOX12B | 242 | 17 | 7975953 | 7991021 |
| 69 | 93 | 61340188 | 61557903 | C20orf20 | 55257 | 20 | 61427804 | 61431945 |
| 69 | 93 | 61340188 | 61557903 | COL9A3 | 1299 | 20 | 61448413 | 61472511 |
| 69 | 93 | 61340188 | 61557903 | DIDO1 | 11083 | 20 | 61518566 | 61557903 |
| 69 | 93 | 61340188 | 61557903 | NTSR1 | 4923 | 20 | 61340188 | 61394123 |
| 69 | 93 | 61340188 | 61557903 | OGFR | 11054 | 20 | 61436176 | 61445352 |
| 69 | 93 | 61340188 | 61557903 | TCFL5 | 10732 | 20 | 61472466 | 61493115 |
| 70 | 92 | 60790016 | 61303647 | ADRM1 | 11047 | 20 | 60878026 | 60883918 |
| 70 | 92 | 60790016 | 61303647 | C20orf151 | 140893 | 20 | 60985292 | 61002629 |
| 70 | 92 | 60790016 | 61303647 | C20orf166 | 128826 | 20 | 61147659 | 61167971 |
| 70 | 92 | 60790016 | 61303647 | C20orf200 | 253868 | 20 | 61141437 | 61148768 |
| 70 | 92 | 60790016 | 61303647 | CABLES2 | 81928 | 20 | 60963685 | 60982339 |
| 70 | 92 | 60790016 | 61303647 | GATA5 | 140628 | 20 | 61038552 | 61051026 |
| 70 | 92 | 60790016 | 61303647 | HRH3 | 11255 | 20 | 60790016 | 60795323 |
| 70 | 92 | 60790016 | 61303647 | LAMA5 | 3911 | 20 | 60884120 | 60942368 |
| 70 | 92 | 60790016 | 61303647 | OSBPL2 | 9885 | 20 | 60813579 | 60871269 |
| 70 | 92 | 60790016 | 61303647 | RPS21 | 6227 | 20 | 60962120 | 60963576 |
| 70 | 92 | 60790016 | 61303647 | SLCO4A1 | 28231 | 20 | 61273796 | 61303647 |
| 71 | 71 | 855483 | 1178237 | GTPBP4 | 23560 | 10 | 1034348 | 1063708 |
| 71 | 71 | 855483 | 1178237 | IDI1 | 3422 | 10 | 1085963 | 1095061 |
| 71 | 71 | 855483 | 1178237 | IDI2 | 91734 | 10 | 1064846 | 1071799 |
| 71 | 71 | 855483 | 1178237 | LARP5 | 23185 | 10 | 855483 | 931702 |
| 71 | 71 | 855483 | 1178237 | WDR37 | 22884 | 10 | 1102775 | 1178237 |
| 72 | 50 | 8152595 | 8193409 | PFAS | 5198 | 17 | 8152595 | 8173809 |
| 72 | 50 | 8152595 | 8193409 | RANGRF | 29098 | 17 | 8191968 | 8193409 |
| 72 | 50 | 8152595 | 8193409 | SLC25A35 | 399512 | 17 | 8191081 | 8198170 |
| 73 | 70 | 320129 | 735608 | DIP2C | 22982 | 10 | 320129 | 735608 |
| 74 | 68 | 92827 | 95178 | RP11- | 347688 | 10 | 92827 | 95178 |

TABLE 1-continued

Locus Rankings. Locus regions within a human prostate tumour genome, the genes contained within each respective locus, the chromosome associated with each gene as well as the start and end nucleotide number associated with each gene on each respective chromosome is shown. Gene regions are based on the hg19 human genome reference (NCBI GRCh37 Genome Reference Consortium Human Reference 37). Each locus, comprised of one or a plurality of genes, is ranked from 1 to 100, based on the Gini Score from the random forest model. Locus rank refers to the order in which they were added to the model.

| Rank | Locus | Locus Start | Locus End | Symbol | EntrezID | Chromosome | Gene Start | Gene End |
|---|---|---|---|---|---|---|---|---|
| 75 | 72 | 1223252 | 1779670 | 631M21.2 ADARB2 | 105 | 10 | 1223252 | 1779670 |
| 76 | 69 | 181423 | 300577 | ZMYND11 | 10771 | 10 | 181423 | 300577 |
| 77 | 28 | 50296853 | 50523781 | ALG12 | 79087 | 22 | 50296853 | 50312106 |
| 77 | 28 | 50296853 | 50523781 | CRELD2 | 79174 | 22 | 50312282 | 50321186 |
| 77 | 28 | 50296853 | 50523781 | IL17REL | 400935 | 22 | 50432941 | 50451055 |
| 77 | 28 | 50296853 | 50523781 | MLC1 | 23209 | 22 | 50497819 | 50523781 |
| 77 | 28 | 50296853 | 50523781 | PIM3 | 415116 | 22 | 50354142 | 50357720 |
| 78 | 36 | 191625 | 256814 | CCDC127 | 133957 | 5 | 204874 | 218297 |
| 78 | 36 | 191625 | 256814 | LOC389257 | 389257 | 5 | 191625 | 195468 |
| 78 | 36 | 191625 | 256814 | SDHA | 6389 | 5 | 218355 | 256814 |
| 79 | 100 | 3541555 | 3688209 | CCDC27 | 148870 | 1 | 3668964 | 3688209 |
| 79 | 100 | 3541555 | 3688209 | KIAA0495 | 57212 | 1 | 3652547 | 3663937 |
| 79 | 100 | 3541555 | 3688209 | TP73 | 7161 | 1 | 3569128 | 3652765 |
| 79 | 100 | 3541555 | 3688209 | TPRG1L | 127262 | 1 | 3541555 | 3546694 |
| 79 | 100 | 3541555 | 3688209 | WDR8 | 49856 | 1 | 3547330 | 3566671 |
| 80 | 88 | 50609159 | 50618724 | PANX2 | 56666 | 22 | 50609159 | 50618724 |
| 81 | 90 | 50883430 | 51066601 | ADM2 | 79924 | 22 | 50919984 | 50924866 |
| 81 | 90 | 50883430 | 51066601 | ARSA | 410 | 22 | 51061181 | 51066601 |
| 81 | 90 | 50883430 | 51066601 | CHKB | 1120 | 22 | 51017386 | 51021428 |
| 81 | 90 | 50883430 | 51066601 | CPT1B | 1375 | 22 | 51007289 | 51016894 |
| 81 | 90 | 50883430 | 51066601 | KLHDC7B | 113730 | 22 | 50986461 | 50989452 |
| 81 | 90 | 50883430 | 51066601 | LMF2 | 91289 | 22 | 50941375 | 50946135 |
| 81 | 90 | 50883430 | 51066601 | MAPK8IP2 | 23542 | 22 | 51041561 | 51049979 |
| 81 | 90 | 50883430 | 51066601 | MIOX | 55586 | 22 | 50925212 | 50928750 |
| 81 | 90 | 50883430 | 51066601 | NCAPH2 | 29781 | 22 | 50946644 | 50958191 |
| 81 | 90 | 50883430 | 51066601 | ODF3B | 440836 | 22 | 50968837 | 50971008 |
| 81 | 90 | 50883430 | 51066601 | SBF1 | 6305 | 22 | 50883430 | 50913464 |
| 81 | 90 | 50883430 | 51066601 | SCO2 | 9997 | 22 | 50961996 | 50964033 |
| 81 | 90 | 50883430 | 51066601 | TYMP | 1890 | 22 | 50964181 | 50968514 |
| 82 | 87 | 50528434 | 50600116 | MOV10L1 | 54456 | 22 | 50528434 | 50600116 |
| 83 | 89 | 50624359 | 50883518 | FAM116B | 414918 | 22 | 50750391 | 50765489 |
| 83 | 89 | 50624359 | 50883518 | HDAC10 | 83933 | 22 | 50683612 | 50689834 |
| 83 | 89 | 50624359 | 50883518 | MAPK11 | 5600 | 22 | 50702141 | 50708779 |
| 83 | 89 | 50624359 | 50883518 | MAPK12 | 6300 | 22 | 50691330 | 50700089 |
| 83 | 89 | 50624359 | 50883518 | PLXNB2 | 23654 | 22 | 50713407 | 50746001 |
| 83 | 89 | 50624359 | 50883518 | RP3-402G11.5 | 83642 | 22 | 50639407 | 50656045 |
| 83 | 89 | 50624359 | 50883518 | SAPS2 | 9701 | 22 | 50781745 | 50883518 |
| 83 | 89 | 50624359 | 50883518 | TRABD | 80305 | 22 | 50624359 | 50638027 |
| 83 | 89 | 50624359 | 50883518 | TUBGCP6 | 85378 | 22 | 50656117 | 50683400 |
| 84 | 60 | 116714117 | 117698807 | BACE1 | 23621 | 11 | 117156401 | 117166386 |
| 84 | 60 | 116714117 | 117698807 | CEP164 | 22897 | 11 | 117198570 | 117283982 |
| 84 | 60 | 116714117 | 117698807 | DSCAML1 | 57453 | 11 | 117298488 | 117667976 |
| 84 | 60 | 116714117 | 117698807 | FXYD2 | 486 | 11 | 117690789 | 117698807 |
| 84 | 60 | 116714117 | 117698807 | KIAA0999 | 23387 | 11 | 116714117 | 116968993 |
| 84 | 60 | 116714117 | 117698807 | PAFAH1B2 | 5049 | 11 | 117014999 | 117047131 |
| 84 | 60 | 116714117 | 117698807 | PCSK7 | 9159 | 11 | 117075787 | 117102811 |
| 84 | 60 | 116714117 | 117698807 | RNF214 | 257160 | 11 | 117103451 | 117156404 |
| 84 | 60 | 116714117 | 117698807 | SIDT2 | 51092 | 11 | 117049938 | 117068161 |
| 84 | 60 | 116714117 | 117698807 | TAGLN | 6876 | 11 | 117070039 | 117075508 |
| 85 | 61 | 117707690 | 117747746 | FXYD6 | 53826 | 11 | 117707690 | 117747746 |
| 86 | 59 | 116618885 | 116708338 | APOA1 | 335 | 11 | 116706468 | 116708338 |
| 86 | 59 | 116618885 | 116708338 | APOA4 | 337 | 11 | 116691417 | 116694011 |
| 86 | 59 | 116618885 | 116708338 | APOA5 | 116519 | 11 | 116660085 | 116663136 |
| 86 | 59 | 116618885 | 116708338 | APOC3 | 345 | 11 | 116700623 | 116703787 |
| 86 | 59 | 116618885 | 116708338 | BUD13 | 84811 | 11 | 116618885 | 116643714 |
| 86 | 59 | 116618885 | 116708338 | ZNF259 | 8882 | 11 | 116649275 | 116658739 |
| 87 | 35 | 47240792 | 47444420 | PREX1 | 57580 | 20 | 47240792 | 47444420 |
| 88 | 31 | 40701391 | 41818557 | PTPRT | 11122 | 20 | 40701391 | 41818557 |
| 89 | 74 | 1461541 | 1524076 | LPCAT1 | 79888 | 5 | 1461541 | 1524076 |
| 90 | 67 | 39314516 | 39317876 | MAFB | 9935 | 20 | 39314516 | 39317876 |
| 91 | 80 | 39657461 | 40247133 | CHD6 | 84181 | 20 | 40031169 | 40247133 |
| 91 | 80 | 39657461 | 40247133 | EMILIN3 | 90187 | 20 | 39988605 | 39995498 |
| 91 | 80 | 39657461 | 40247133 | LPIN3 | 64900 | 20 | 39969559 | 39989222 |
| 91 | 80 | 39657461 | 40247133 | PLCG1 | 5335 | 20 | 39766160 | 39804357 |
| 91 | 80 | 39657461 | 40247133 | TOP1 | 7150 | 20 | 39657461 | 39753126 |
| 91 | 80 | 39657461 | 40247133 | ZHX3 | 23051 | 20 | 39807088 | 39928739 |
| 92 | 83 | 42219578 | 42345122 | IFT52 | 51098 | 20 | 42219578 | 42275862 |
| 92 | 83 | 42219578 | 42345122 | MYBL2 | 4605 | 20 | 42295708 | 42345122 |
| 93 | 86 | 47538274 | 47653230 | ARFGEF2 | 10564 | 20 | 47538274 | 47653230 |

TABLE 1-continued

Locus Rankings. Locus regions within a human prostate tumour genome, the genes contained within each respective locus, the chromosome associated with each gene as well as the start and end nucleotide number associated with each gene on each respective chromosome is shown. Gene regions are based on the hg19 human genome reference (NCBI GRCh37 Genome Reference Consortium Human Reference 37). Each locus, comprised of one or a plurality of genes, is ranked from 1 to 100, based on the Gini Score from the random forest model. Locus rank refers to the order in which they were added to the model.

| Rank | Locus | Locus Start | Locus End | Symbol | EntrezID | Chromosome | Gene Start | Gene End |
|---|---|---|---|---|---|---|---|---|
| 94 | 85 | 44650328 | 45035271 | CD40 | 958 | 20 | 44746905 | 44758384 |
| 94 | 85 | 44650328 | 45035271 | CDH22 | 64405 | 20 | 44802375 | 44880334 |
| 94 | 85 | 44650328 | 45035271 | ELMO2 | 63916 | 20 | 44994689 | 45035271 |
| 94 | 85 | 44650328 | 45035271 | NCOA5 | 57727 | 20 | 44689625 | 44718580 |
| 94 | 85 | 44650328 | 45035271 | SLC12A5 | 57468 | 20 | 44650328 | 44688789 |
| 94 | 85 | 44650328 | 45035271 | SLC35C2 | 51006 | 20 | 44978176 | 44993064 |
| 95 | 65 | 46130600 | 46285621 | NCOA3 | 8202 | 20 | 46130600 | 46285621 |
| 96 | 81 | 42086503 | 42170535 | L3MBTL | 26013 | 20 | 42136319 | 42170535 |
| 96 | 81 | 42086503 | 42170535 | SFRS6 | 6431 | 20 | 42086503 | 42092244 |
| 97 | 82 | 42193754 | 42214273 | SGK2 | 10110 | 20 | 42193754 | 42214273 |
| 98 | 64 | 45129706 | 45985474 | EYA2 | 2139 | 20 | 45523262 | 45817492 |
| 98 | 64 | 45129706 | 45985474 | SLC13A3 | 64849 | 20 | 45186461 | 45280100 |
| 98 | 64 | 45129706 | 45985474 | SLC2A10 | 81031 | 20 | 45338278 | 45364985 |
| 98 | 64 | 45129706 | 45985474 | TP53RK | 112858 | 20 | 45313003 | 45318276 |
| 98 | 64 | 45129706 | 45985474 | ZMYND8 | 23613 | 20 | 45838380 | 45985474 |
| 98 | 64 | 45129706 | 45985474 | ZNF334 | 55713 | 20 | 45129706 | 45142194 |
| 99 | 66 | 46286149 | 46415360 | SULF2 | 55959 | 20 | 46286149 | 46415360 |
| 100 | 84 | 42354800 | 42698254 | GTSF1L | 149699 | 20 | 42354800 | 42355642 |
| 100 | 84 | 42354800 | 42698254 | TOX2 | 84969 | 20 | 42544781 | 42698254 |

TABLE 2

Copy Number Alterations (CNA) Regions that have been observed in high grade prostate tumours.

| Region | Type | IGRT rank | RP rank | Genes in region (genes with most CNAs, or genes with known or putative cancer assocations) |
|---|---|---|---|---|
| 8p21.3 | Del | 1 | 5 | PEBP4, RHOBTB2, TNFRSF10B, TNFRSF10C, TNFRSF10D, TNFRSF10A, CHMP7, LOXL2, ENTPD4 |
| 8P11.22 | Del | 42 | 1 | FGFR1, C8orf86 |
| 8p23.1 | Del | 2 | 2 | DEFB103A, DEFB103B, SPAG11B, DEFB104A, DEFB104B, DEFB106A, DEFB106B, DEFB105A, DEFB105B, DEFB107A, DEFB107B, SPAG11A, DEFB4 |
| 8p22.1 | Del | 3 | 3 | NKX3-1, STC1 |
| 8q24.3 | Amp | 29 | 78 | COL22AI KCNK9 TRAPPC9 CHRAC1 EIF2C2 PTK2 DENND3 SLC45A4 GPR20 PTP4A3 FLJ43860 TSNARE1 BAIIARC JRK PSCA LY6K C8orf55 SLURP1 LYPD2 LYNX1 LY6D GML |
| 8q21.2 | Amp | 7 | 167 | REXOIL1 |
| 16q22.2 | Del | 16 | 9 | HP, HPR, TXNL4B, DHX38, PMFBP1, ZFHX3 |
| 16q23.2 | Del | 6 | 52 | WWOX, MAF, DYNLRB2, CDYL2, C16orf6J, CENPN, ATMIN, C16orf46, GCSH, PKDIL2, BCMOI, GAN, CMIP |
| 6q15 | Del | 13 | 17 | MAP3K7, BACH2 |
| 15q11 | Del | 16 | 60 | LRCH1 ESD HTR2A SUCLA2 NUDT15 MED4 ITM2BRB1 P2RY5 RCBTB2 CYSLTR2 FNDC3A MLNR CDADC1 CAB39LSETDB2 PHF11 RCBTB1 ARL11 EBPL KPNA3 C13orf1 TRIM3 KCNRG |

TABLE 3

Regions of the genome with a CNA in the majority of patients from Subtype 1. A deletion is encoded by -1, and an amplification by 1, in the 'CNA Change' column.

| Chromosome | Chromosome Nucleotide Start | Chromosome Nucleotide End | CNA Change | Genes |
|---|---|---|---|---|
| 6 | 87647023 | 87726397 | -1 | HTR1E |
| 6 | 90142896 | 91296907 | -1 | ANKRD6, LYRM2, MDN1, CASP8AP2, GJA10, BACH2, MAP3K7 |
| 7 | 18535884 | 20700017 | 1 | HDAC9, TWIST1, FERD3L, TWISTNB, TMEM196, MACC1, ITGB8, ABCB5 |
| 7 | 21467688 | 39747723 | 1 | SP4, DNAH11, CDCA7L, RAPGEF5, IL6, TOMM7, FAM126A, KLHL7, NUPL2, GPNMB, C7orf30, IGF2BP3, TRA2A, CCDC126, C7orf46, STK31, NPY, MPP6, DFNA5, OSBPL3, CYCS, C7orf31, NPVF, NFE2L3, HNRNPA2B1, CBX3, SNX10, SKAP2, HOXA1, HOXA2, HOXA3, HOXA4, HOXA5, HOXA6, HOXA7, HOXA9, HOXA10, HOXA11, HOXA13, EVX1, HIBADH, |

TABLE 3-continued

Regions of the genome with a CNA in the majority of patients from Subtype 1. A deletion is encoded by −1, and an amplification by 1, in the 'CNA Change' column.

| Chromosome | Chromosome Nucleotide Start | Chromosome Nucleotide End | CNA Change | Genes |
|---|---|---|---|---|
| | | | | TAX1BP1, JAZF1, CREB5, KIAA0644, CPVL, CHN2, PRR15, WIPF3, SCRN1, FKBP14, PLEKHA8, C7orf41, ZNRF2, NOD1, GGCT, GARS, CRHR2, INMT, C7orf67, AQP1, GHRHR, ADCYAP1R1, NEUROD6, CCDC129, C7orf16, PDE1C, LSM5, AVL9, KBTBD2, FKBP9, NT5C3, RP9, BBS9, BMPER, NPSR1, DPY19L1, TBX20, HERPUD2, SEPT7, EEPD1, KIAA0895, ANLN, AOAH, ELMO1, GPR141, TXNDC3, SFRP4, EPDR1, STARD3NL, TARP, AMPH, FAM183B, VPS41, POU6F2, C7orf36, RALA |
| 7 | 42000547 | 42977453 | 1 | GLI3, C7orf25, PSMA2, MRPL32 |
| 7 | 45927958 | 45960871 | 1 | IGFBP1, IGFBP3 |
| 7 | 97736196 | 99573735 | 1 | LMTK2, BHLHA15, TECPR1, BRI3, BAIAP2L1, NPTX2, TMEM130, TRRAP, SMURF1, ARPC1A, ARPC1B, PDAP1, BUD31, PTCD1, CPSF4, ATP5J2, ZNF789, ZNF394, ZKSCAN5, C7orf38, ZNF655, ZNF498, CYP3A5, CYP3A7, CYP3A4, CYP3A43, OR2AE1, TRIM4, GJC3, AZGP1 |
| 7 | 128784711 | 129691233 | 1 | TSPAN33, SMO, AHCYL2, FAM40B, NRF1, UBE2H, ZC3HC1 |
| 7 | 135046546 | 135433594 | 1 | CNOT4, NUP205, SLC13A4, FAM180A |
| 7 | 141251077 | 143748430 | 1 | AGK, KIAA1147, WEE2, SSBP1, TAS2R3, TAS2R4, TAS2R5, LOC136242, OR9A4, CLEC5A, TAS2R38, MGAM, TRYX3, PRSS1, PRSS2, EPHB6, TRPV6, TRPV5, C7orf34, KEL, OR9A2, OR6V1, PIP, TAS2R39, TAS2R40, GSTK1, TMEM139, CASP2, CLCN1, FAM131B, ZYX, EPHA1, TAS2R60, TAS2R41, LOC441294, FAM115C, CTAGE6, FAM115A, OR2F2, OR2F1, OR6B1, OR2A5 |
| 7 | 144149033 | 144533146 | 1 | TPK1 |
| 7 | 149128453 | 151217010 | 1 | ZNF777, ZNF746, ZNF767, KRBA1, ZNF467, SSPO, ZNF862, ATP6V0E2, LRRC61, C7orf29, RARRES2, REPIN1, ZNF775, GIMAP8, GIMAP7, GIMAP4, GIMAP6, GIMAP2, GIMAP1, GIMAP5, TMEM176B, TMEM176A, ABP1, KCNH2, NOS3, ATG9B, ABCB8, ACCN3, CDK5, SLC4A2, FASTK, TMUB1, AGAP3, GBX1, ASB10, ABCF2, CSGLCA-T, SMARCD3, NUB1, WDR86, CRYGN, RHEB |
| 7 | 153749776 | 156685902 | 1 | DPP6, PAXIP1, HTR5A, INSIG1, EN2, CNPY1, RBM33, SHH, RNF32, LMBR1 |
| 7 | 157129710 | 158937649 | 1 | DNAJB6, PTPRN2, NCAPG2, FAM62B, WDR60, VIPR2 |
| 8 | 16884746 | 24367077 | −1 | EFHA2, ZDHHC2, CNOT7, VPS37A, MTMR7, SLC7A2, PDGFRL, MTUS1, FGL1, PCM1, ASAH1, NAT1, NAT2, PSD3, SH2D4A, CSGALNACT1, INTS10, LPL, SLC18A1, ATP6V1B2, LZTS1, GFRA2, DOK2, XPO7, NPM2, FGF17, EPB49, FAM160B2, NUDT18, HR, REEP4, LGI3, SFTPC, BMP1, PHYHIP, POLR3D, PIWIL2, SLC39A14, PPP3CC, SORBS3, PDLIM2, C8orf58, KIAA1967, BIN3, EGR3, PEBP4, RHOBTB2, TNFRSF10B, TNFRSF10C, TNFRSF10D, TNFRSF10A, CHMP7, LOXL2, ENTPD4, SLC25A37, NKX3-1, STC1, ADAM28, ADAMDEC1, ADAM7 |
| 8 | 132916355 | 139926236 | 1 | EFR3A, OC90, KCNQ3, LRRC6, TMEM71, PHF20L1, TG, SLA, WISP1, NDRG1, ST3GAL1, ZFAT, KHDRBS3, FAM135B, COL22A1 |
| 20 | 55743808 | 60640866 | 1 | BMP7, SPO11, RAE1, RBM38, CTCFL, PCK1, ZBP1, PMEPA1, C20orf85, RAB22A, VAPB, APCDD1L, STX16, NPEPL1, GNAS, TH1L, CTSZ, TUBB1, ATP5E, SLMO2, ZNF831, EDN3, PHACTR3, SYCP2, PPP1R3D, C20orf177, CDH26, C20orf197, CDH4, TAF4 |

TABLE 4

Regions of the genome with a CNA in the majority of patients from Subtype 2. A deletion is encoded by −1, and an amplification by 1, in the 'CNA Change' column.

| Chromosome | Chromosome Nucleotide Start | Chromosome Nucleotide End | CNA Change | Genes |
|---|---|---|---|---|
| 3 | 122628039 | 134979307 | 1 | SEMA5B, PDIA5, SEC22A, ADCY5, PTPLB, MYLK, CCDC14, ROPN1, KALRN, UMPS, ITGB5, MUC13, HEG1, SLC12A8, ZNF148, SNX4, OSBPL11, ALG1L, ROPN1B, SLC41A3, ALDH1L1, KLF15, CCDC37, ZXDC, UROC1, CHST13, C3orf22, TR2IT1, CHCHD6, PLXNA1, GPR175, MCM2, PODXL2, ABTB1, MGLL, KLHDC6, SEC61A1, RUVBL1, EEFSEC, DNAJB8, GATA2, C3orf27, RPN1, RAB7A, ACAD9, KIAA1257, CCDC48, GP9, RAB43, ISY1, CNBP, COPG, C3orf37, H1FX, C3orf25, |

TABLE 4-continued

Regions of the genome with a CNA in the majority of patients from Subtype 2. A deletion is encoded by −1, and an amplification by 1, in the 'CNA Change' column.

| Chromosome | Chromosome Nucleotide Start | Chromosome Nucleotide End | CNA Change | Genes |
|---|---|---|---|---|
| | | | | MBD4, IFT122, RHO, H1FOO, PLXND1, TMCC1, TRH, COL29A1, COL6A6, PIK3R4, ATP2C1, ASTE1, NEK11, NUDT16, MRPL3, CPNE4, ACPP, DNAJC13, ACAD11, CCRL1, UBA5, NPHP3, TMEM108, BFSP2, CDV3, TOPBP1, TF, SRPRB, RAB6B, C3orf36, SLCO2A1, RYK, AMOTL2, ANAPC13, CEP63, KY, EPHB1 |
| 3 | 137483133 | 137752494 | 1 | SOX14, CLDN18 |
| 3 | 139062860 | 141331197 | 1 | MRPS22, COPB2, RBP2, RBP1, NMNAT3, CLSTN2, TRIM42, SLC25A36, SPSB4, ACPL2, ZBTB38, RASA2 |
| 3 | 142536701 | 143567373 | 1 | PCOLCE2, PAQR9, SR140, CHST2, SLC9A9 |
| 3 | 156544095 | 157319021 | 1 | LEKR1, CCNL1, PTX3, VEPH1, C3orf55 |
| 3 | 157827891 | 161221730 | 1 | RSRC1, MLF1, GFM1, LXN, RARRES1, MFSD1, IQCJ, SCHIP1, IL12A, IFT80, SMC4, TRIM59, KPNA4, ARL14, PPM1L, B3GALNT1, NMD3, C3orf57, OTOL1 |
| 6 | 82455446 | 119256327 | −1 | FAM46A, IBTK, TPBG, UBE2CBP, DOPEY1, PGM3, RWDD2A, ME1, PRSS35, SNAP91, RIPPLY2, CYB5R4, MRAP2, KIAA1009, TBX18, NT5E, SNX14, SYNCRIP, HTR1E, CGA, ZNF292, GJB7, C6orf162, C6orf165, SLC35A1, RARS2, ORC3L, AKIRIN2, SPACA1, CNR1, RNGTT, PNRC1, SRrp35, PM20D2, GABRR1, GABRR2, UBE2J1, RRAGD, ANKRD6, LYRM2, MDN1, CASP8AP2, GJA10, BACH2, MAP3K7, EPHA7, MANEA, FUT9, KIAA0776, FHL5, GPR63, NDUFAF4, KLHL32, C6orf167, POU3F2, FBXL4, C6orf168, COQ3, SFRS18, USP45, CCNC, PRDM13, MCHR2, SIM1, ASCC3, GRIK2, HACE1, LIN28B, BVES, POPDC3, PREP, PRDM1, ATG5, AIM1, RTN4IP1, QRSL1, C6orf203, BEND3, PDSS2, SOBP, SCML4, SEC63, OSTM1, NR2E1, SNX3, LACE1, FOX03, ARMC2, SESN1, C6orf182, CD164, PPIL6, SMPD2, MICAL1, ZBTB24, AKD2, FIG4, GPR6, WASF1, CDC40, DDO, SLC22A16, CDC2L6, AMD1, GTF3C6, BXDC1, SLC16A10, KIAA1919, REV3L, TRAF3IP2, FYN, WISP3, TUBE1, C6orf225, LAMA4, RFPL4B, MARCKS, HDAC2, HS3ST5, FRK, NT5DC1, COL10A1, TSPYL4, TSPYL1, DSE, FAM26F, FAM26E, FAM26D, RWDD1, RSPH4A, ZUFSP, KPNA5, FAM162B, GPRC6A, RFX6, VGLL2, ROS1, DCBLD1, GOPC, NUS1, SLC35F1, C6orf204, PLN, ASF1A, MCM9 |
| 8 | 116085 | 38070819 | −1 | OR4F21, ZNF596, FBXO25, C8orf42, ERICH1, DLGAP2, CLN8, ARHGEF10, KBTBD11, MYOM2, CSMD1, MCPH1, ANGPT2, AGPAT5, XKR5, DEFB1, DEFA6, DEFA4, DEFA1, LOC728358, DEFA3, DEFA5, DEFB103A, DEFB103B, SPAG11B, DEFB104A, DEFB104B, DEFB106A, DEFB106B, DEFB105A, DEFB105B, DEFB107A, DEFB107B, SPAG11A, DEFB4, PRAGMIN, CLDN23, MFHAS1, ERI1, PPP1R3B, TNKS, MSRA, UNQ9391, RP1L1, C8orf74, SOX7, PINX1, XKR6, MTMR9, AMAC1L2, FAM167A, BLK, GATA4, NEIL2, FDFT1, CTSB, DEFB137, DEFB136, DEFB134, DEFB130, ZNF705D, DUB3, FAM86B1, LONRF1, C8orf79, DLC1, SGCZ, TUSC3, MSR1, FGF20, EFHA2, ZDHHC2, CNOT7, VPS37A, MTMR7, SLC7A2, PDGFRL, MTUS1, FGL1, PCM1, ASAH1, NAT1, NAT2, PSD3, SH2D4A, CSGALNACT1, INTS10, LPL, SLC18A1, ATP6V1B2, LZTS1, GFRA2, DOK2, XPO7, NPM2, FGF17, EPB49, FAM160B2, NUDT18, HR, REEP4, LGI3, SFTPC, BMP1, PHYHIP, POLR3D, PIWIL2, SLC39A14, PPP3CC, SORBS3, PDLIM2, C8orf58, KIAA1967, BIN3, EGR3, PEBP4, RHOBTB2, TNFRSF10B, TNFRSF10C, TNFRSF10D, TNFRSF10A, CHMP7, LOXL2, ENTPD4, SLC25A37, NKX3-1, STC1, ADAM28, ADAMDEC1, ADAM7, NEFM, NEFL, DOCK5, GNRH1, KCTD9, CDCA2, EBF2, PPP2R2A, BNIP3L, PNMA2, DPYSL2, ADRA1A, STMN4, TRIM35, PTK2B, CHRNA2, EPHX2, CLU, SCARA3, CCDC25, ESCO2, PBK, SCARA5, C8orf80, ELP3, PNOC, ZNF395, FBXO16, FZD3, EXTL3, INTS9, HMBOX1, KIF13B, DUSP4, TMEM66, LEPROTL1, DCTN6, RBPMS, GTF2E2, GSR, UBXN8, PPP2CB, TEX15, PURG, WRN, NRG1, FUT10, MAK16, C8orf41, RNF122, DUSP26, UNC5D, KCNU1, ZNF703, ERLIN2, PROSC, GPR124, BRF2, RAB11FIP1, GOT1L1, ADRB3, EIF4EBP1, ASH2L, STAR, LSM1, BAG4 |
| 8 | 41119475 | 41368499 | −1 | SFRP1, GOLGA7 |
| 8 | 58907112 | 70747299 | 1 | FAM110B, UBXN2B, CYP7A1, SDCBP, NSMAF, TOX, CA8, RAB2A, CHD7, RLBP1L1, ASPH, NKAIN3, GGH, TTPA, YTHDF3, BHLHE22, CYP7B1, ARMC1, MTFR1, PDE7A, DNAJC5B, TRIM55, CRH, RRS1, ADHFE1, C8orf46, MYBL1, VCPIP1, C8orf44, SGK3, C8orf45, LRRC67, COPS5, CSPP1, ARFGEF1, CPA6, PREX2, C8orf34, SULF1, SLCO5A1 |

TABLE 4-continued

Regions of the genome with a CNA in the majority of patients from Subtype 2. A deletion is encoded by −1, and an amplification by 1, in the 'CNA Change' column.

| Chromosome | Chromosome Nucleotide Start | Chromosome Nucleotide End | CNA Change | Genes |
|---|---|---|---|---|
| 8 | 72753776 | 74005507 | 1 | MSC, TRPA1, KCNB2, TERF1, C8orf84 |
| 8 | 75736771 | 75946793 | 1 | PI15, CRISPLD1 |
| 8 | 77593514 | 146176274 | 1 | ZFHX4, PXMP3, PKIA, FAM164A, IL7, STMN2, HEY1, MRPS28, TPD52, ZBTB10, ZNF704, PAG1, FABP5, PMP2, FABP9, FABP4, FABP12, IMPA1, SLC10A5, ZFAND1, CHMP4C, SNX16, RALYL, LRRCC1, E2F5, C8orf59, CA13, CA1, CA3, CA2, REXO1L1, PSKH2, ATP6V0D2, SLC7A13, WWP1, FAM82B, CPNE3, CNGB3, CNBD1, WDR21C, MMP16, RIPK2, OSGIN2, NBN, DECR1, CALB1, TMEM64, NECAB1, TMEM55A, OTUD6B, SLC26A7, RUNX1T1, FAM92A1, RBM12B, TMEM67, PPM2C, CDH17, GEM, RAD54B, KIAA1429, ESRP1, DPY19L4, INTS8, CCNE2, TP53INP1, C8orf38, PLEKHF2, C8orf37, GDF6, UQCRB, MTERFD1, PTDSSI, SDC2, PGCP, TSPYL5, MTDH, LAPTM4B, MATN2, RPL30, C8orf47, HRSP12, POP1, NIPAL2, KCNS2, STK3, OSR2, VPS13B, COX6C, RGS22, FBXO43, POLR2K, SPAG1, RNF19A, ANKRD46, SNX31, PABPC1, YWHAZ, ZNF706, GRHL2, NCALD, RRM2B, UBR5, ODF1, KLF10, AZIN1, ATP6V1C1, BAALC, FZD6, CTHRC1, SLC25A32, WDSOF1, RIMS2, TM7SF4, DPYS, LRP12, ZFPM2, OXR1, ABRA, ANGPT1, RSPO2, EIF3E, TTC35, TMEM74, TRHR, NUDCD1, ENY2, PKHD1L1, EBAG9, GOLSYN, KCNV1, CSMD3, TRPS1, EIF3H, UTP23, RAD21, C8orf85, SLC30A8, MED30, EXT1, SAMD12, TNFRSF11B, COLEC10, MAL2, NOV, ENPP2, TAF2, DSCC1, DEPDC6, COL14A1, MRPL13, MTBP, SNTB1, HAS2, ZHX2, DERL1, WDR67, FAM83A, C8orf76, ZHX1, ATAD2, WDYHV1, FBXO32, KLHL38, ANXA13, FAM91A1, FER1L6, TMEM65, TRMT12, RNF139, TATDN1, NDUFB9, MTSS1, ZNF572, SQLE, KIAA0196, NSMCE2, TRIB1, FAM84B, MYC, GSDMC, FAM49B, ASAP1, ADCY8, EFR3A, OC90, KCNQ3, LRRC6, TMEM71, PHF20L1, TG, SLA, WISP1, NDRG1, ST3GAL1, ZFAT, KHDRBS3, FAM135B, COL22A1, KCNK9, TRAPPC9, CHRAC1, EIF2C2, PTK2, DENND3, SLC45A4, GPR20, PTP4A3, FLJ43860, TSNARE1, BAI1, ARC, JRK, PSCA, LY6K, C8orf55, SLURP1, LYPD2, LYNX1, LY6D, GML, CYP11B1, CYP11B2, LY6E, C8orf31, LY6H, GPIHBP1, ZFP41, GLI4, ZNF696, TOP1MT, RHPN1, MAFA, ZC3H3, GSDMD, C8orf73, NAPRT1, EEF1D, TIGD5, PYCRL, TSTA3, ZNF623, ZNF707, MAPK15, FAM83H, SCRIB, PUF60, NRBP2, EPPK1, PLEC1, PARP10, GRINA, SPATC1, OPLAH, EXOSC4, GPAA1, CYC1, SHARPIN, MAF1, C8orf30A, HEATR7A, SCXB, BOP1, HSF1, DGAT1, SCRT1, FBXL6, GPR172A, ADCK5, CPSF1, SLC39A4, VPS28, NFKBIL2, CYHR1, KIFC2, FOXH1, PPP1R16A, GPT, MFSD3, RECQL4, LRRC14, LRRC24, C8orf82, K1AA1688, ZNF251, ZNF34, RPL8, ZNF517, ZNF7, COMMD5, ZNF250, ZNF16 |
| 13 | 36050885 | 53626196 | −1 | NBEA, DCLK1, SOHLH2, SPG20, CCNA1, C13orf36, RFXAP, SMAD9, ALG5, EXOSC8, FAM48A, CSNK1A1L, POSTN, TRPC4, UFM1, FREM2, STOML3, C13orf23, NHLRC3, LHFP, COG6, FOXO1, MRPS31, SLC25A15, ELF1, WBP4, KBTBD6, KBTBD7, MTRF1, NARG1L, C13orf15, KIAA0564, DGKH, AKAP11, TNFSF11, C13orf30, EPSTI1, DNAJC15, ENOX1, CCDC122, C13orf31, SERP2, TSC22D1, NUFIP1, KIAA1704, GTF2F2, KCTD4, TPT1, SLC25A30, COG3, SPERT, SIAH3, ZC3H13, CPB2, LCP1, C13orf18, LRCH1, ESD, HTR2A, SUCLA2, NUDT15, MED4, ITM2B, RB1, P2RY5, RCBTB2, CYSLTR2, FNDC3A, MLNR, CDADC1, CAB39L, SETDB2, PHF11, RCBTB1, ARL11, EBPL, KPNA3, C13orf1, TRIM13, KCNRG, DLEU7, RNASEH2B, FAM124A, SERPINE3, INTS6, WDFY2, DHRS12, CCDC70, ATP7B, ALG11, UTP14C, NEK5, NEK3, THSD1, VPS36, CKAP2, HNRNPA1L2, SUGT1, LECT1, PCDH8, OLFM4 |
| 16 | 78133326 | 81324747 | −1 | WWOX, MAF, DYNLRB2, CDYL2, C16orf61, CENPN, ATMIN, C16orf46, GCSH, PKD1L2, BCMO1 |

TABLE 5

Regions of the genome with a CNA in the majority of patients from Subtype 3. A deletion is encoded by −1, and an amplification by 1, in the 'CNA Change' column.

| Chromosome | Chromosome Nucleotide Start | Chromosome Nucleotide End | CNA Change | Genes |
|---|---|---|---|---|
| 8 | 182383 | 30041155 | −1 | ZNF596, FBXO25, C8orf42, ERICH1, DLGAP2, CLN8, ARHGEF10, KBTBD11, MYOM2, CSMD1, MCPH1, ANGPT2, AGPAT5, XKR5, DEFB1, DEFA6, DEFA4, DEFA1, LOC728358, DEFA3, DEFA5, DEFB103A, DEFB103B, SPAG11B, DEFB104A, DEFB104B, DEFB106A, DEFB106B, DEFB105A, DEFB105B, DEFB107A, DEFB107B, SPAG11A, DEFB4, PRAGMIN, CLDN23, MFHAS1, ERI1, PPP1R3B, TNKS, MSRA, UNQ9391, RP1L1, C8orf74, SOX7, PINX1, XKR6, MTMR9, AMAC1L2, FAM167A, BLK, GATA4, NEIL2, FDFT1, CTSB, DEFB137, DEFB136, DEFB134, DEFB130, ZNF705D, DUB3, FAM86B1, LONRF1, C8orf79, DLC1, SGCZ, TUSC3, MSR1, FGF20, EFHA2, ZDHHC2, CNOT7, VPS37A, MTMR7, SLC7A2, PDGFRL, MTUS1, FGL1, PCM1, ASAH1, NAT1, NAT2, PSD3, SH2D4A, CSGALNACT1, INTS10, LPL, SLC18A1, ATP6V1B2, LZTS1, GFRA2, DOK2, XPO7, NPM2, FGF17, EPB49, FAM160B2, NUDT18, HR, REEP4, LGI3, SFTPC, BMP1, PHYHIP, POLR3D, PIWIL2, SLC39A14, PPP3CC, SORBS3, PDLIM2, C8orf58, KIAA1967, BIN3, EGR3, PEBP4, RHOBTB2, TNFRSF10B, TNFRSF10C, TNFRSF10D, TNFRSF10A, CHMP7, LOXL2, ENTPD4, SLC25A37, NKX3-1, STC1, ADAM28, ADAMDEC1, ADAM7, NEFM, NEFL, DOCK5, GNRH1, KCTD9, CDCA2, EBF2, PPP2R2A, BNIP3L, PNMA2, DPYSL2, ADRA1A, STMN4, TRIM35, PTK2B, CHRNA2, EPHX2, CLU, SCARA3, CCDC25, ESCO2, PBK, SCARA5, C8orf80, ELP3, PNOC, ZNF395, FBXO16, FZD3, EXTL3, INTS9, HMBOX1, KIF13B, DUSP4, TMEM66, LEPROTL1, DCTN6 |
| 8 | 31497267 | 41909505 | −1 | NRG1, FUT10, MAK16, C8orf41, RNF122, DUSP26, UNC5D, KCNU1, ZNF703, ERLIN2, PROSC, GPR124, BRF2, RAB11FIP1, GOT1L1, ADRB3, EIF4EBP1, ASH2L, STAR, LSM1, BAG4, DDHD2, PPAPDC1B, WHSC1L1, LETM2, FGFR1, C8orf86, TACC1, PLEKHA2, HTRA4, TM2D2, ADAM9, ADAM32, ADAM18, ADAM2, IDO1, IDO2, C8orf4, ZMAT4, SFRP1, GOLGA7, GINS4, AGPAT6, NKX6-3, ANK1, MYST3 |
| 16 | 56659584 | 58328951 | −1 | MT1E, MT1M, MT1A, MT1B, MT1F, MT1G, MT1H, MT1X, NUP93, SLC12A3, HERPUD1, CETP, NLRC5, CPNE2, NIP30, RSPRY1, ARL2BP, PLLP, CCL22, CX3CL1, CCL17, CIAPIN1, COQ9, POLR2C, DOK4, CCDC102A, GPR114, GPR56, GPR97, CCDC135, KATNB1, KIFC3, CNGB1, TEPP, ZNF319, C16orf57, MMP15, C16orf80, CSNK2A2, CCDC113, KLKBL4 |
| 16 | 66836780 | 89556969 | −1 | NAE1, CA7, PDP2, CDH16, RRAD, FAM96B, CES2, CES3, CES8, CBFB, C16orf70, B3GNT9, TRADD, FBXL8, HSF4, NOL3, KIAA0895L, EXOC3L, E2F4, ELMO3, LRRC29, TMEM208, FHOD1, SLC9A5, PLEKHG4, KCTD19, LRRC36, TPPP3, ZDHHC1, HSD11B2, ATP6V0D1, AGRP, FAM65A, CTCF, RLTPR, ACD, PARD6A, C16orf48, C16orf86, GFOD2, RANBP10, TSNAXIP1, CENPT, THAP11, NUTF2, EDC4, NRN1L, PSKH1, CTRL, PSMB10, LCAT, SLC12A4, DPEP3, DPEP2, DDX28, DUS2L, NFATC3, ESRP2, PLA2G15, SLC7A6, SLC7A6OS, PRMT7, SMPD3, ZFP90, CDH3, CDH1, TMCO7, HAS3, CHTF8, CIRH1A, SNTB2, VPS4A, PDF, COG8, NIP7, TMED6, TERF2, CYB5B, NFAT5, NQO1, NOB1, WWP2, CLEC18A, PDPR, CLEC18C, EXOSC6, AARS, DDX19B, DDX19A, ST3GAL2, FUK, COG4, SF3B3, IL34, MTSS1L, VAC14, HYDIN, FTSJD1, CALB2, ZNF23, ZNF19, CHST4, TAT, MARVELD3, PHLPPL, AP1G1, ZNF821, KIAA0174, DHODH, HP, HPR, TXNL4B, DHX38, PMFBP1, ZFHX3, HTA, PSMD7, CLEC18B, GLG1, RFWD3, MLKL, FA2H, WDR59, ZNRF1, LDHD, ZFP1, CTRB2, CTRB1, BCAR1, CFDP1, TMEM170A, CHST6, CHST5, FLJ22167, GABARAPL2, ADAT1, KARS, TERF2IP, CNTNAP4, MON1B, ADAMTS18, NUDT7, VAT1L, CLEC3A, WWOX, MAF, DYNLRB2, CDYL2, C16orf61, CENPN, ATMIN, C16orf46, GCSH, PKD1L2, BCMO1, GAN, CMIP, PLCG2, SDR42E1, HSD17B2, MPHOSPH6, CDH13, HSBP1, MLYCD, OSGIN1, NECAB2, SLC38A8, MBTPS1, HSDL1, LRRC50, TAF1C, ADAD2, KCNG4, WFDC1, ATP2C2, KIAA1609, COTL1, KLHL36, USP10, CRISPLD2, ZDHHC7, KIAA0513, FAM92B, KIAA0182, GINS2, C16orf74, COX4NB, COX4I1, IRF8, FOXF1, MTHFSD, FOXC2, FOXL1, FBXO31, MAP1LC3B, ZCCHC14, JPH3, KLHDC4, SLC7A5, CA5A, BANP, ZFPM1, ZC3H18, IL17C, CYBA, MVD, SNAI3, RNF166, C16orf84, CDT1, APRT, GALNS, TRAPPC2L, LOC390748, CBFA2T3, ACSF3, CDH15, ZNF778, ANKRD11 |

TABLE 6

Prognosis of proposed biomarkers and clinical variables. PGA: Percent Genome Alteration; AUC: Area Under the receiver operator Curve; HR: Hazard Ratio a

| | Toronto-IGRT | | MSKCC full | | Cambridge full | |
| --- | --- | --- | --- | --- | --- | --- |
| | Univariate | Multivariate | Univariate | Multivariate | Univariate | Multivariate |
| Gleason 7 vs. 5-6 | 1.0 (0.44-2.4; 0.95) | 1.0 (0.44-2.5; 0.92) | 3.4 (1.5-8.0; 0.0044) | 2.8 (1.2-6.7I 0.019) | 6.2 (0.82-47; 0.078) | 5.6 (0.74-43; 0.95) |
| Gleason 8-9 vs. 5-6 | NA | NA | 7.3 (2.9-18; <0.0001) | 4.9 (1.8-13I 0.0015) | 8.1 (0.85-78; 0.069) | 5.7 (0.58-56; 0.14) |
| PSA (continuous) | 1.2 (1.1-1.3; 0.0012) | NA* | 1.006 (1.003-1.009; 0.00030) | NA* | 1.1 (1.0-1.2; 0.063) | NA* |
| T2 vs. T1** | 0.82 (0.39-1.7; 0.60) | 0.86 (0.40-1.8; 0.69) | NA | NA | NA | NA |
| T3 vs. T1-2** | NA | NA | 9.2 (4.1-21; <0.0001) | 6.1 (2.6-14; <0.0001) | 2.8 (1.0-7.8; 0.50) | 3.6 (1.2-11; 0.024) |
| NCCN int. vs. low | 1.4 (0.43-4.7; 0.57) | NA | 2.5 (0.80-7.9I 0.12) | NA | 2.2 (0.28-18; 0.45) | NA |
| NCCN high vs. low | NA | NA | 12.6 (4.3-37; <0.0001) | NA | 6.9 (0.88-55; 0.66) | NA | b

| | Toronto-IGRT | | MSKCC full | | Cambridge full | |
| --- | --- | --- | --- | --- | --- | --- |
| | Univariate | Multivariate | Univariate | Multivariate | Univariate | Multivariate |
| PGA ≥7.49 vs. PGA <7.49 HR (p) | 4.2 (2.0-8.9; 0.00019) | 4.5 (2.1-9.8; 0.00013) | 3.8 (<0.0001) | 3.4 (1.6-7.2; 0.0011) | 3.8 (1.4-9.9; 0.0075) | 3.2 (1.1-9.0; 0.029) |
| PGA (continuous) HR (p) | 1.05 (1.03-1.08I <0.0001) | 1.06 (1.03-1.09; 0.00019) | 1.15 (0.0054) | 1.05 (1.0-1.1; 0.065) | 1.09 (1.0-1.2; 0.0020) | 1.08 (1.0-1.1; 0.0012) |
| AUC | 0.71 (0.66-0.77) | 0.70 (0.65-0.76) | 0.49 (0.44-0.54) | 0.82 (0.76-0.88) | 0.70 (0.63-0.77) | 0.66 (0.58-0.73) |
| C-index | 0.72 (0.64-0.81) | 0.70 (0.60-.079) | 0.60 (0.48-0.72) | 0.71 (0.63-0.80) | 0.65 (0.50-0.70) | 0.72 (0.72-0.61) | c

| Hypoxic measure: | Toronto-IGRT | Pooled RadP full | | |
| --- | --- | --- | --- | --- |
| | HP20 | Buffa | West | Winter |
| +/+ vs. −/− HR (p) | 11 (2.4-47; 0.0018) | 2.3 (1.1-4.8; 0.031) | 5.3 (1.8-16; 0.0027) | 2.6 (1.1-5.9; 0.025) |
| AUC | 0.67 (0.61-0.73) | 0.58 (0.53-0.64) | 0.59 (0.54-0.65) | 0.53 (0.47-0.58) |
| C-index | 0.67 (0.59-0.75) | 0.62 (0.54-0.71) | 0.65 (0.58-0.73) | 0.64 (0.55-0.73) | d

| | MSKCC full | | Cambridge full | |
| --- | --- | --- | --- | --- |
| | Univariate | Multivariate | Univariate | Multivariate |
| 100-loci DNA signature HR (p) | 4.0 (0.00011) | 2.8 (1.4-6.0; 0.0060) | 2.9 (1.1-8.2; 0.038) | 2.9 (1.0-8.2; 0.046) |
| AUC | 0.74 (0.68-0.80) | 0.84 (0.78-0.89) | 0.64 (0.57-0.71) | 0.75 (0.68-0.83) |
| C-index | 0.70 (0.61-0.80) | 0.74 (0.65-0.83) | 0.67 (0.54-0.79) | 0.73 (0.62-0.85) | a) The HR and p values ("HR (p)") from Cox proportional hazard models are shown for each prognostic clinical variables in the univariate and multivariate setting for each full cohort. Multivariate models include Gleason Score, PSA and T-category only (NCCN is not included). The multivariate models show the covariates and levels used for multivariate analysis of biomarkers throughout the study. *PSA is stratified at 10 ng/mL since it fails the proportional hazards assumption. **For the Toronto-IGRT cohort where there are only low-int patients, we compare T2 to T1 patients, whereas for the RadP cohorts, T3 patients are compared to T1-2 patients.
b) The HR and p-value are provided for dichotomized and continuous PGA in each cohort, based on Cox proportional hazard models including only the marker of interest ("Univariate") and models including relevant clinical covariates as in the multivariate models in table 2A ("Multivariate"). The AUC and C-index are provided for the continuous PGA values.
c) HR, p-values, AUC, and C-index values for patients stratified by PGA and hypoxia. The Cox proportional hazard model was fit with four levels (PGA/Hypoxia: +/+, +/−, −/+, and −/−), with −/− patients used as the baseline group. Hazard ratios are not adjusted for clinical variables and the pooled RadP cohorts are shown for all three RNA hypoxia signatures.
d) The HR and p-value are provided for the 100-loci DNA signature in each full validation cohort, based on Cox proportional hazard models including only the marker of interest ("Univariate") and models including relevant clinical covariates as in the multivariate models in table 2A ("Multivariate"). The AUC and C-index are provided for the continuous Signature Risk Score.

TABLE 7

Common Classification Systems of Prostate Cancer Risk. There are five common classification systems used to clinically stratify prostate cancer patients into low, intermediate and high risk groups: NCCN, D'Amico, GUROC, CAPSURE and ESMO. Each of these will stratify prostate cancer patients as low-, intermediate- or high-risk based on Gleason score, pre-treatment PSA and T-catergory. The Gleason score is obtained from the diagnostic biopsy, and determined by a pathologist. The T-category is related to the size and spread of the tumour within the prostate and surrounding area, as determined by a digital rectum exam and imaging tests. PSA is a blood-based biomarker, measured in ng/mL.

| Classification System | Low-Risk Localized Prostate Cancer | Intermediate risk localized prostate cancer | High risk localized prostate cancer |
|---|---|---|---|
| D'Amico | T1-T2a and GS ≤6 and PSA ≤10 | T2b and/or GS = 7 and/or PSA >10-20 not low-risk | ≥T2c or PSA >20 or GS 8-10 |
| GUROC (Genitourinary Radiation Oncologists of Canada) | T1-T2a and GS ≤6 and PSA ≤10 | T1-T2 and/or Gleason ≤7 and/or PSA ≤20 not low-risk | ≥T3a or PSA >20 or GS 8-10 |
| CAPSURE (Cancer of the Prostate Strategic Urologic Research Endeavour) | T1-T2a and GS ≤6 and PSA ≤10 | T2b and/or GS = 7 and/or PSA >10-20 not low-risk | T3-4 or PSA >20 or GS 8-10 |
| NCCN (National Comprehensive Cancer Network) | T1-T2a and GS 2-6 and PSA ≤10 not very low risk AND very-low risk category: T1c and GS ≤6 and PSA <10 and fewer than 3 biopsy cores positive and ≤50% cancer in each core | T2b or T2c and/or GS = 7 and/or PSA >10-20 not low-risk | T3a or PSA >20 or GS 8-10 not very high risk AND very high-risk category: T3b-4 |
| ESMO (European Association of Urology) | T1-T2a and GS ≤6 and PSA <10 | Not high risk and not low risk (the remainder) | T3-4 or PSA >20 or GS 8-10 |

REFERENCE LIST

Baca, S. C., Prandi, D., Lawrence, M. S., Mosquera, J. M., Romanel, A., Drier, Y., Park, K., et al. (2013). Punctuated Evolution of Prostate Cancer Genomes. Cell, 153(3), 666-677. doi:10.1016/j.cell.2013.03.021.

Boormans J L, Korsten H, Ziel-van der Made A J, van Leenders G J, de vos C V, Jenster G, et al. Identification of TDRD1 as a direct target gene of ERG in primary prostate cancer. Int J Cancer (2013); 133: 335-45.

Boutros, P. C., Lau, S. K., Pintilie, M., Liu, N., Shepherd, F. a, Der, S. D., Tsao, M.-S., et al. (2009). Prognostic gene signatures for non-small-cell lung cancer. Proceedings of the National Academy of Sciences of the United States of America, 106(8), 2824-8. doi:10.1073/pnas.0809444106

Breiman, L. (2001). Random forest. Machine Learning, 45(1), 5-32. doi:10.1016/j.compbiomed.2011.03.001

Bristow, R. G., & Hill, R. P. (2008). Hypoxia and metabolism. Hypoxia, DNA repair and genetic instability. Nature reviews. Cancer, 8(3), 180-92. doi:10.1038/nrc2344

Buffa F M, Harris A L, West C M, C J Miller. Large meta-analysis of multiple cancers reveals a common, compact and highly prognostic hypoxia metagene. Brit. J. Cancer 2010; 102: 428-35.

Buyyounouski, M. K., Pickles, T., Kestin, L. L., Allison, R., & Williams, S. G. (2012). Validating the interval to biochemical failure for the identification of potentially lethal prostate cancer. Journal of clinical oncology, 30(15), 1857-63. doi:10.1200/JCO.2011.35.1924

Chin, L., Andersen, J. N., & Futreal, P. A. (2011). Cancer genomics: from discovery science to personalized medicine. Nature medicine, 17(3), 297-303. doi:10.1038/nm.2323

Cuzick, J, Berney, D. M., Fisher, G., Mesher, D., Møller, H., Reid, J. E., Perry, M., et al. (2012). Prognostic value of a cell cycle progression signature for prostate cancer death in a conservatively managed needle biopsy cohort. British journal of cancer, 106(6), 1095-9. doi:10.1038/bjc.2012.39

Cuzick, Jack, Swanson, G. P., Fisher, G., Brothman, A. R., Berney, D. M., Reid, J. E., Mesher, D., et al. (2011). Prognostic value of an RNA expression signature derived from cell cycle proliferation genes in patients with prostate cancer: a retrospective study. The lancet oncology, 12(3), 245-55. doi:10.1016/S1470-2045(10)70295-3

Dal Pra, A., Lalonde, E., Srigley, J., Squire, J., Joshua, A., Petrovics, G., Boutros, P. C., et al. (2013). TMPRSS2-ERG Status Is Not Prognostic Following Prostate Cancer Radiotherapy: Implications for Fusion Status and DSB Repair. Clinical Cancer Research.

D'Amico, A. V. D., Moul, J., Carroll, P. R., Sun, L., Lubeck, D., & Chen, M. (2003). Cancer-Specific Mortality After Surgery or Radiation for Patients With Clinically Localized Prostate Cancer Managed During the Prostate-Specific Antigen Era, 21(11), 2163-2172. doi:10.1200/JCO.2003.01.075.

Den R, Feng F Y, Showalter T N, et al. The Decipher prostate cancer classifier predicts biochemical failure in patients following post-operative radiation therapy. Presented at SUO Annual Meeting, Bethesda, 2013.

Dunning M J, Smith M L, Ritchie M E, Tavare S. et al. beadarray: R classes and methods for Illumina bead-based data. *Bioinformatics* 2007; 23: 2183-2184.

Erho N, Crisan A, Vergara I A, Mitra A P, Ghadessi M, Buerki C, et al. Discovery and validation of a prostate cancer genomic classifier that predicts early metastasis following radical prostatectomy. *PLoS One* 2013; 8: e66855.

Eustace A, Mani N, Span P N, Joely J I, Taylor J, Betts G N J, et al. A 26-gene hypoxia signature predicts benefit from hypoxia-modifying therapy in laryngeal cancer but not bladder cancer. *Clin. Cancer Res.* 2013; 19: 4879-88.

Freedland, S. J., Humphreys, E. B., Mangold, L. A., Eisenberger, M., Dorey, F. J., Walsh, P. C., & Partin, A. W. (2005). Risk of Prostate Cancer—Specific Mortality Following Biochemical Recurrence After Radical Prostatectomy, 294(4), 433-439.

Fritz V, Benfodda Z, Henriquet C, et al. Metabolic intervention on lipid synthesis converging pathways abrogates prostate cancer growth. *Oncogene* 2013; 32(42): 5101-10.

Goodwin J F, Schiewer M J, Dean J L, et al. A Hormone-DNA Repair Circuit Governs the Response to Genotoxic Insult. *Cancer discovery* 2013; 3(11): 1254-71.

Heagerty, P. J., Lumley, T., & Pepe, M. S. (2000). Time-Dependent ROC Curves for Censored Survival Data and a Diagnostic Marker, (June), 337-344.

Helpap, B., Ringli, D., Shaikhibrahim, Z., Wernert, N., & Kristiansen, G. (2013). The heterogeneous Gleason 7 carcinoma of the prostate: analyses of low and high grade (risk) carcinomas with criteria of the International Society of Urological Pathology (ISUP). *Pathology, research and practice*, 209(3), 190-4. doi: 10.1016/j.prp.2012.10.016

Ishkanian, A. S., Mallof, C. a, Ho, J., Meng, A., Albert, M., Syed, A., van der Kwast, T., et al. (2009). High-resolution array CGH identifies novel regions of genomic alteration in intermediate-risk prostate cancer. *The Prostate*, 69(10), 1091-100. doi:10.1002/pros.20959

Jaccard, P. (1901). Étude comparative de la distribution florale dans une portion des Alpes et des Jura. *Bulletin de la Société Vaudoise des Sciences Naturelles*, 37, 547-579.

Jhavar S, Brewer D, Edwards S, Kote-Jarai Z, Attard G, Clark J, et al. Integration of ERG gene mapping and gene-expression profiling identifies distinct categories of human prostate cancer. *BJU Int* 2009; 103: 1256-69.

Johnson W E, Li C, Rabinovic A, Tavare S. Adjusting batch effects in microarray expression data using empirical Bayes methods. *Biostatistics* 2007; 8: 118-127.

Johnson, S., Jackson, W., Li, D., Song, Y., Foster, C., Foster, B., Zhou, J., et al. (2013). The interval to biochemical failure is prognostic for metastasis, prostate cancer-specific mortality, and overall mortality after salvage radiation therapy for prostate cancer. *International journal of radiation oncology, biology, physics*, 86(3), 554-61. doi: 10.1016/j.ijrobp.2013.02.016

Kapadia, N. S., Olson, K., Sandler, H. M., Feng, F. Y., & Hamstra, D. a. (2012). Interval to biochemical failure as a biomarker for cause-specific and overall survival after dose-escalated external beam radiation therapy for prostate cancer. *Cancer*, 118(8), 2059-68. doi:10.1002/cncr.26498

Karnes J R, Bergstralh E J, Davicioni E, Ghadessi M, Buerki C, Mitra A P, et al. Validation of a genomic classifier that predicts metastasis following radical prostatectomy in an at risk patient population. *J Urol* 2013; 190: 2047-53.

Khojasteh, M., Lam, W. L., Ward, R. K., & MacAulay, C. (2005). A stepwise framework for the normalization of array CGH data. *BMC bioinformatics*, 6, 274. doi: 10.1186/1471-2105-6-274

Liu, W., Chang, B., Cramer, S., Koty, P. P., Li, T., Sun, J., Turner, A. R., et al. (2007). Deletion of a Small Consensus Region at 6q15, Including the MAP3K7 Gene, Is Significantly Associated with High-Grade Prostate Cancers High-Grade Prostate Cancers, 5028-5033. doi:10.1158/1078-0432.CCR-07-0300

Locke, J. a, Zafarana, G., Ishkanian, A. S., Milosevic, M., Thoms, J., Have, C. L., Malloff, C. a, et al. (2012). NKX3.1 haploinsufficiency is prognostic for prostate cancer relapse following surgery or image-guided radiotherapy. *Clinical cancer research: an official journal of the American Association for Cancer Research*, 18(1), 308-16. doi:10.1158/1078-0432.CCR-11-2147

Locke, J. a, Zafarana, G., Malloff, C. a, Lam, W. L., Sykes, J., Pintilie, M., Ramnarine, V. R., et al. (2012). Allelic loss of the loci containing the androgen synthesis gene, StAR, is prognostic for relapse in intermediate-risk prostate cancer. *The Prostate*, 72(12), 1295-305. doi:10.1002/pros.22478.

Magi-Galluzzi C, Li J, Stephenson A J, et al. Independent validation of a genomic classifier in an at risk population of men conservatively managed after radical prostatectomy. Presented at SUO Annual Meeting, Bethesda, 2013.

Markert, E. K., Mizuno, H., Vazquez, A., & Levine, A. J. (2011). Molecular classification of prostate cancer using curated expression signatures. PNAS.

Menon S, Manning B D. Common corruption of the mTOR signaling network in human tumors. *Oncogene* 2008; 27(2): S43-51.

Milosevic M, Chung P, Parker C, et al. Androgen withdrawal in patients reduces prostate cancer hypoxia: implications for disease progression and radiation response. *Cancer Res* 2007; 67(13): 6022-5.

Milosevic, M., Warde, P., Ménard, C., Chung, P., Toi, A., Ishkanian, A., McLean, M., et al. (2012). Tumor hypoxia predicts biochemical failure following radiotherapy for clinically localized prostate cancer. *Clinical cancer research: an official journal of the American Association for Cancer Research*, 18(7), 2108-14. doi:10.1158/1078-0432.CCR-11-2711

Minner, S., Enodien, M., Sirma, H., Luebke, A. M., Krohn, A., Mayer, P. S., Simon, R., et al. (2011). ERG status is unrelated to PSA recurrence in radically operated prostate cancer in the absence of antihormonal therapy. *Clinical cancer research: an official journal of the American Association for Cancer Research*, 17(18), 5878-88. doi:10.1158/1078-0432.CCR-11-1251

Mohler, J. L., Armstrong, A. J., Bahnson, R. R., Boston, B., Busby, J. E., D'Amico, A. V., Eastham, J. a, et al. (2012). Prostate Cancer, Version 3.2012 Featured Updates to the NCCN Guidelines. *Journal of the National Comprehensive Cancer Network: JNCCN*, 10(9), 1081-1087. Retrieved from http://www.ncbi.nlm.nih.gov/pubmed/22956807

Nichol, A. M., Warde, P., & Bristow, R. G. (2005). Optimal treatment of intermediate-risk prostate carcinoma with radiotherapy: clinical and translational issues. *Cancer,* 104(5), 891-905. doi:10.1002/cncr.21257

Parker C, Milosevic M, Toi A, Sweet J, Panzarella T, Bristow R G, Catton C, Catton, P, Crook J, Gospodarowicz M, McLean M, Warde P and Hill RadP. A polarographic electrode study of tumour oxygenation in clinically localized prostate cancer. International Journal of Radiation Oncology Biology Physics, 58, 750-757 (2004).

Penney, K. L., Sinnott, J. a, Fall, K., Pawitan, Y., Hoshida, Y., Kraft, P., Stark, J. R., et al. (2011). mRNA expression signature of Gleason grade predicts lethal prostate cancer. *Journal of clinical oncology: official journal of the American Society of Clinical Oncology,* 29(17), 2391-6. doi: 10.1200/JCO.2010.32.6421.

Piccolo S R, Withers M R, Francis O E, Bild A H, Johnson W E. Multiplatform single-sample estimates of transcriptional activation. *Proc Natl Acad Sci USA* 2013; 110: 17778-83.

Polyak, K., & Garber, J. (2011). Targeting the missing links for cancer therapy. *Nature medicine,* 17(3), 283-4. doi: 10.1038/nm0311-283.

Prensner J R, Rubin M A, Wei J T, Chinnaiyan A M. Beyond PSA: The Next Generation of Prostate Cancer Biomarkers. *Sci Transl Med* 2012; 4(127): 127rv3.

Roach, M., Hanks, G., Thames, H., Schellhammer, P., Shipley, W. U., Sokol, G. H., & Sandler, H. (2006). Defining biochemical failure following radiotherapy with or without hormonal therapy in men with clinically localized prostate cancer: recommendations of the RTOG-ASTRO Phoenix Consensus Conference. *International journal of radiation oncology, biology, physics,* 65(4), 965-74. doi: 10.1016/j.ijrobp.2006.04.029

Sebastiani, P., Kohane, I. S., & Ramoni, M. F. (2003). Consensus Subtypeing: A Resampling-Based Method for Class Discovery and Visualization of Gene, (i), 91-118.

Shah, S. P., Xuan, X., DeLeeuw, R. J., Khojasteh, M., Lam, W. L., Ng, R., & Murphy, K. P. (2006). Integrating copy number polymorphisms into array CGH analysis using a robust HMM. *Bioinformatics (Oxford, England),* 22(14), e431-9. doi:10.1093/bioinformatics/btl238

Shao, Y.-H., Demissie, K., Shih, W., Mehta, A. R., Stein, M. N., Roberts, C. B., Dipaola, R. S., et al. (2009). Contemporary risk profile of prostate cancer in the United States. *Journal of the National Cancer Institute,* 101(18), 1280-3. doi:10.1093/jnci/djp262

Shen, M. M., & Abate-shen, C. (2010). Molecular genetics of prostate cancer: new prospects for old challenges. *Genes & Development,* (212), 1967-2000. doi:10.1101/gad.1965810.GENES Spratt, D. E., Zumsteg, Z., Ghadjar, P., Pangasa, M., Pei, X., Fine, S. W., Yamada, Y., et al. (2013). Prognostic importance of Gleason 7 disease among patients treated with external beam radiation therapy for prostate cancer: results of a detailed biopsy core analysis. *International journal of radiation oncology, biology, physics,* 85(5), 1254-61. doi:10.1016/j.ijrobp.2012.10.013

Starmans, M. H. W., Fung, G., Steck, H., Wouters, B. G., & Lambin, P. (2011). A simple but highly effective approach to evaluate the prognostic performance of gene expression signatures. *PloS one,* 6(12), e28320. doi:10.1371/journal.pone.0028320

Stratton, M. R., Campbell, P. J., & Futreal, P. A. (2009). The cancer genome. *Nature,* 458(7239), 719-24. doi:10.1038/nature07943

Taylor, B. S., Schultz, N., Hieronymus, H., Gopalan, A., Xiao, Y., Carver, B. S., Arora, V. K., et al. (2010). Integrative genomic profiling of human prostate cancer. *Cancer cell,* 18(1), 11-22. doi:10.1016/j.ccr.2010.05.026

Tran, B., Dancey, J. E., Kamel-Reid, S., McPherson, J. D., Bedard, P. L., Brown, A. M. K., Zhang, T., et al. (2012). Cancer genomics: technology, discovery, and translation. *Journal of clinical oncology: official journal of the American Society of Clinical Oncology,* 30(6), 647-60. doi: 10.1200/JCO.2011.39.2316

Turaka, A., Buyyounouski, M. K., Hanlon, A. L., Horwitz, E. M., Greenberg, R. E., & Movsas, B. (2012). Hypoxic prostate/muscle PO2 ratio predicts for outcome in patients with localized prostate cancer: long-term results. *International journal of radiation oncology, biology, physics,* 82(3), e433-9. doi:10.1016/j.ijrobp.2011.05.037

Venet, D., Dumont, J. E., & Detours, V. (2011). Most random gene expression signatures are significantly associated with breast cancer outcome. *PLoS computational biology,* 7(10), e1002240. doi:10.1371/journal.pcbi.1002240

Vergis, R., Corbishley, C. M., Norman, A. R., Bartlett, J., Jhavar, S., Borre, M., Heeboll, S., et al. (2008). Intrinsic markers of tumour hypoxia and angiogenesis in localised prostate cancer and outcome of radical treatment: a retrospective analysis of two randomised radiotherapy trials and one surgical cohort study. *The lancet oncology,* 9(4), 342-51. doi:10.1016/S1470-2045(08)70076-7

Warren A Y, Whitaker H C, Haynes B, Sangan T, McDuffus L A, Kay J D, et al. Method for sampling tissue for research which preserves pathological data in radical prostatectomy. Prostate 2013; 73: 194-202.

Winter S C, Buffa F M, Silva P, Crispin Miller, Valentine H R, Turley H, et al. Relation of a hypoxia metagene derived from head and neck cancer to prognosis of multiple cancers. *Cancer Res.* 2007; 67: 3441-9.

Wouters, B. G., & Koritzinsky, M. (2008). Hypoxia signalling through mTOR and the unfolded protein response in cancer. *Nature reviews. Cancer,* 8(11), 851-64. doi: 10.1038/nrc2501

Wu, C.-L., Schroeder, B. E., Ma, X.-J., Cutie, C. J., Wu, S., Salunga, R., Zhang, Y., et al. (2013). Development and validation of a 32-gene prognostic index for prostate cancer progression. *Proceedings of the National Academy of Sciences of the United States of America,* 110(15), 6121-6. doi:10.1073/pnas.1215870110

Yau C, Mouradov D, Jorissen R N, Colella S, Ghazala M, Steers G, et al. A statistical approach for detecting genomic aberrations in heterogeneous tumor samples from single nucleotide polymorphism genotyping data. *Genome Biol* 2010; 11: R92.

Young R M, Ackerman D, Quinn Z L, et al. Dysregulated mTORC1 renders cells critically dependent on desaturated lipids for survival under tumor-like stress. *Genes Dev* 2013; 27(10): 1115-31.

Yue S, Li J, Lee S-Y, et al. Cholesteryl Ester Accumulation Induced by PTEN Loss and PI3K/AKT Activation Underlies Human Prostate Cancer Aggressiveness. *Cell Metab* 2014; 19(3): 393-406.

Zafarana, G., Ishkanian, A. S., Malloff, C. a, Locke, J. a, Sykes, J., Thoms, J., Lam, W. L., et al. (2012). Copy number alterations of c-MYC and PTEN are prognostic factors for relapse after prostate cancer radiotherapy. *Cancer.*

The invention claimed is:

1. A method for treating a patient for cancer, the method comprising administering adjuvant therapy to the patient, wherein the patient's risk of cancer recurrence had been determined by:

(a) obtaining a biopsy of the tumour;
(b) identifying genome regions of the biopsy wherein the regions are at least the following loci: nucleotides 21549529 to 21645346 of chromosome 8; nucleotides 40962149 to 41065386 of chromosome 17; nucleotides 8559665 to 8890849 of chromosome 8; nucleotides 113139327 to 113242481 of chromosome 13; nucleotides 131265453 to 131978646 of chromosome 10; nucleotides 136469715 to 136659848 of chromosome 8; nucleotides 135490030 to 135725292 of chromosome 8; nucleotides 83637442 to 84746935 of chromosome 10; nucleotides 90640025 to 90775542 of chromosome 10; nucleotides 90579658 to 90611732 of chromosome 10; nucleotides 8175257 to 8239257 of chromosome 8; nucleotides 7305275 to 7754237 of chromosome 8; nucleotides 8993763 to 9009152 of chromosome 8; nucleotides 43511808 to 43586893 of chromosome 19; nucleotides 7286415 to 7740105 of chromosome 8; nucleotides 191625 to 256814 of chromosome 13; nucleotides 48972117 to 49147744 of chromosome 22; nucleotides 149570056 to 149577787 of chromosome 7; nucleotides 149535508 to 149564568 of chromosome 7; nucleotides 47158517 to 47571342 of chromosome 22; nucleotides 149473130 to 149531053 of chromosome 7; nucleotides 12869772 to 12887284 of chromosome 8; nucleotides 12579405 to 12612992 of chromosome 8; nucleotides 88744089 to 88781786 of chromosome 16; nucleotides 88003623 to 88601574 of chromosome 16; nucleotides 90033620 to 90343082 of chromosome 10; nucleotides 88636788 to 88729495 of chromosome 16; nucleotides 9413444 to 9639856 of chromosome 8; nucleotides 72937384 to 73024522 of chromosome 3; nucleotides 87863628 to 87970112 of chromosome 16; nucleotides 111530886 to 111567416 of chromosome 13; nucleotides 42607779 to 42623929 of chromosome 8; nucleotides 11141999 to 11189695 of chromosome 8; nucleotides 90965693 to 90967071 of chromosome 10; nucleotides 90346518 to 90537999 of chromosome 10; nucleotides 116638561 to 117072975 of chromosome 9; nucleotides 42396938 to 42408140 of chromosome 8; nucleotides 11994676 to 12051624 of chromosome 8; nucleotides 11921897 to 11973025 of chromosome 8; nucleotides 1201709 to 1295162 of chromosome 5; nucleotides 1317999 to 1345002 of chromosome 5; nucleotides 1392904 to 1445543 of chromosome 5; nucleotides 60697516 to 60777810 of chromosome 20; nucleotides 42010463 to 42065194 of chromosome 8; nucleotides 42249278 to 42397068 of chromosome 8;
(c) determining a plurality of copy number calls in the genome regions;
(d) intersecting the plurality of copy number calls with a reference gene list, to obtain a plurality of Copy Number Alterations (CNA) calls for each gene;
(e) generating a CNA tumour profile based on the plurality of CNA calls;
(f) comparing the CNA tumour profile to a reference profile of recurring cancer patients and a reference profile of nonrecurring cancer patients;
(g) calculating a plurality of statistical distances between the CNA tumour profile and the reference profile of recurring cancer patients and the reference profile of nonrecurring cancer patients;
wherein the statistical distance between the CNA tumour profile and the reference profile of recurring cancer patients and the reference profile of nonrecurring cancer patients is associated with the risk of cancer recurrence following the cancer therapy of the patient.

2. The method of claim 1, wherein the genome regions additionally include at least the following groups of loci:
(a) nucleotides 42195972 to 42234674 of chromosome 8; nucleotides 1009167 to 1112172 of chromosome 5; nucleotides 443333 to 467409 of chromosome 5; nucleotides 50166936 to 50218452 of chromosome 22; nucleotides 56725982 to 57290900 of chromosome 20;
(b) nucleotides 42195972 to 42234674 of chromosome 8; nucleotides 1009167 to 1112172 of chromosome 5; nucleotides 443333 to 467409 of chromosome 5; nucleotides 50166936 to 50218452 of chromosome 22; nucleotides 56725982 to 57290900 of chromosome 20; nucleotides 135170364 to 135290723 of chromosome 5; nucleotides 11700033 to 11853760 of chromosome 8; nucleotides 271735 to 443258 of chromosome 5; nucleotides 11561716 to 11696818 of chromosome 8; nucleotides 57466425 to 57617901 of chromosome 20; nucleotides 612404 to 693510 of chromosome 5; nucleotides 473333 to 524549 of chromosome 5; nucleotides 795719 to 892939 of chromosome 5; nucleotides 892968 to 918164 of chromosome 5; nucleotides 113845796 to 114466484 of chromosome 11; nucleotides 60549853 to 60640866 of chromosome 20; nucleotides 50247496 to 50283726 of chromosome 22; nucleotides 7942357 to 7952451 of chromosome 17; nucleotides 7905987 to 7923658 of chromosome 17; nucleotides 7999217 to 8151413 of chromosome 17; nucleotides 7623038 to 7853237 of chromosome 17; nucleotides 1568824 to 1599179 of chromosome 10; nucleotides 7975953 to 7991021 of chromosome 17; nucleotides 61340188 to 61557903 of chromosome 20; nucleotides 60790016 to 61303647 of chromosome 20;
(c) nucleotides 42195972 to 42234674 of chromosome 8; nucleotides 1009167 to 1112172 of chromosome 5; nucleotides 443333 to 467409 of chromosome 5; nucleotides 50166936 to 50218452 of chromosome 22; nucleotides 56725982 to 57290900 of chromosome 20; nucleotides 135170364 to 135290723 of chromosome 5; nucleotides 11700033 to 11853760 of chromosome 8; nucleotides 271735 to 443258 of chromosome 5; nucleotides 11561716 to 11696818 of chromosome 8; nucleotides 57466425 to 57617901 of chromosome 20; nucleotides 612404 to 693510 of chromosome 5; nucleotides 473333 to 524549 of chromosome 5; nucleotides 795719 to 892939 of chromosome 5; nucleotides 892968 to 918164 of chromosome 5; nucleotides 113845796 to 114466484 of chromosome 11; nucleotides 60549853 to 60640866 of chromosome 20; nucleotides 50247496 to 50283726 of chromosome 22; nucleotides 7942357 to 7952451 of chromosome 17; nucleotides 7905987 to 7923658 of chromosome 17; nucleotides 7999217 to 8151413 of chromosome 17; nucleotides 7623038 to 7853237 of chromosome 17; nucleotides 1568824 to 1599179 of chromosome 10; nucleotides 7975953 to 7991021 of chromosome 17; nucleotides 61340188 to 61557903 of chromosome 20; nucleotides 60790016 to 61303647 of chromosome 20; nucleotides 855483 to 1178237 of chromosome 10; nucleotides 8152595 to 8193409 of chromosome 17; nucleotides 320129 to 735608 of chromosome 10; nucleotides 92827 to 95178 of chromosome 10; nucleotides 1223252 to 1779670 of chromosome 10; nucleotides 181423 to 300577 of chromosome 10;

nucleotides 50296853 to 50523781 of chromosome 22; nucleotides 191625 to 256814 of chromosome 5; nucleotides 3541555 to 3688209 of chromosome 1; nucleotides 50609159 to 50618724 of chromosome 22; nucleotides 50883430 to 51066601 of chromosome 22; nucleotides 50528434 to 50600116 of chromosome 22; nucleotides 50624359 to 50883518 of chromosome 22; nucleotides 116714117 to 117698807 of chromosome 11; nucleotides 117707690 to 117747746 of chromosome 11; nucleotides 116618885 to 116708338 of chromosome 11; nucleotides 47240792 to 47444420 of chromosome 20; nucleotides 40701391 to 41818557 of chromosome 20; nucleotides 1461541 to 1524076 of chromosome 5; nucleotides 39314516 to 39317876 of chromosome 20;

(d) nucleotides 42195972 to 42234674 of chromosome 8; nucleotides 1009167 to 1112172 of chromosome 5; nucleotides 443333 to 467409 of chromosome 5; nucleotides 50166936 to 50218452 of chromosome 22; nucleotides 56725982 to 57290900 of chromosome 20; nucleotides 135170364 to 135290723 of chromosome 5; nucleotides 11700033 to 11853760 of chromosome 8; nucleotides 271735 to 443258 of chromosome 5; nucleotides 11561716 to 11696818 of chromosome 8; nucleotides 57466425 to 57617901 of chromosome 20; nucleotides 612404 to 693510 of chromosome 5; nucleotides 473333 to 524549 of chromosome 5; nucleotides 795719 to 892939 of chromosome 5; nucleotides 892968 to 918164 of chromosome 5; nucleotides 113845796 to 114466484 of chromosome 11; nucleotides 60549853 to 60640866 of chromosome 20; nucleotides 50247496 to 50283726 of chromosome 22; nucleotides 7942357 to 7952451 of chromosome 17; nucleotides 7905987 to 7923658 of chromosome 17; nucleotides 7999217 to 8151413 of chromosome 17; nucleotides 7623038 to 7853237 of chromosome 17; nucleotides 1568824 to 1599179 of chromosome 10; nucleotides 7975953 to 7991021 of chromosome 17; nucleotides 61340188 to 61557903 of chromosome 20; nucleotides 60790016 to 61303647 of chromosome 20; nucleotides 855483 to 1178237 of chromosome 10; nucleotides 8152595 to 8193409 of chromosome 17; nucleotides 320129 to 735608 of chromosome 10; nucleotides 92827 to 95178 of chromosome 10; nucleotides 1223252 to 1779670 of chromosome 10; nucleotides 181423 to 300577 of chromosome 10; nucleotides 50296853 to 50523781 of chromosome 22; nucleotides 191625 to 256814 of chromosome 5; nucleotides 3541555 to 3688209 of chromosome 1; nucleotides 50609159 to 50618724 of chromosome 22; nucleotides 50883430 to 51066601 of chromosome 22; nucleotides 50528434 to 50600116 of chromosome 22; nucleotides 50624359 to 50883518 of chromosome 22; nucleotides 116714117 to 117698807 of chromosome 11; nucleotides 117707690 to 117747746 of chromosome 11; nucleotides 116618885 to 116708338 of chromosome 11; nucleotides 47240792 to 47444420 of chromosome 20; nucleotides 40701391 to 41818557 of chromosome 20; nucleotides 1461541 to 1524076 of chromosome 5; nucleotides 39314516 to 39317876 of chromosome 20; nucleotides 39657461 to 40247133 of chromosome 20; nucleotides 42219578 to 42345122 of chromosome 20; nucleotides 47538274 to 47653230 of chromosome 20; nucleotides 44650328 to 45035271 of chromosome 20; nucleotides 46130600 to 46285621 of chromosome 20; nucleotides 42086503 to 42170535 of chromosome 20; nucleotides 42193754 to 42214273 of chromosome 20; nucleotides 45129706 to 45985474 of chromosome 20; nucleotides 46286149 to 46415360 of chromosome 20; nucleotides 42354800 to 42698254 of chromosome 20.

3. The method of claim 1, wherein the genome regions are a whole tumour genome.

4. The method according claim 1, wherein the patient has been diagnosed with prostate cancer.

5. The method according to claim 1, wherein the patient has been diagnosed with localized prostate cancer.

6. The method according to claim 1, wherein the patient has one of a low or intermediate risk prostate cancer prognosis.

7. The method according to claim 6, wherein the patient has one of a low or intermediate risk prostate cancer prognosis as determined by at least one of T-category, Gleason score or pre-treatment prostate-specific antigen blood concentration.

8. The method according to claim 6, wherein the low risk for prostate cancer is determined by at least one of the following:
(a) a T-category of T1-T2a, a Gleason score less than or equal to 6, and a pre-treatment prostate-specific antigen blood concentration less than or equal to 10 ng/mL;
(b) a T-category of T1-T2a, a Gleason score greater than or equal to 2 and less than or equal to 6, and a pre-treatment prostate-specific antigen blood concentration less than or equal to 10 ng/mL; and
(c) a T-category of T1c, a Gleason score less than or equal to 6, a pre-treatment prostate-specific antigen blood concentration less than or equal to 10 ng/mL, and fewer than 3 biopsy cores of a tumour that are positive for cancer and having less than or equal to 50% cancer in each.

9. The method according to claim 6, wherein the intermediate risk prostate cancer prognosis had been determined by at least one of the following:
(a) at least one of a T-category of T2b, a Gleason score equal to 7, and a pre-treatment prostate-specific antigen blood concentration greater than 10 ng/mL;
(b) at least one of a T-category of T1-T2, a Gleason score equal to or less than 7, and a pre-treatment prostate-specific antigen blood concentration less than or equal to 20 ng/mL;
(c) at least one of a T-category of T2b, a Gleason score equal to 7 and a pre-treatment prostate-specific antigen blood concentration greater than 10 ng/ml and equal to or less than 20 ng/mL; and
(d) at least one of a T-category of T2b, a T-category of T2c, a Gleason score equal to 7 and a pre-treatment prostate-specific antigen blood concentration greater than 10 ng/ml and equal to or less than 20 ng/mL.

10. The method according to claim 1, wherein determining the risk of recurrence further comprised determining hypoxia levels in the biopsy.

11. The method according to claim 1, wherein the biopsy is obtained before the administering step.

12. The method according to claim 1, further comprising treatment of the patient with at least one of image-guided radiotherapy or radical prostatectomy.

13. A method for treating a patient for cancer, the method comprising administering a combination of localized and systemic therapy to a patient, wherein the patient's risk of cancer recurrence had been determined by:
(a) obtaining a biopsy of the tumour;
(b) identifying genome regions of the biopsy wherein the regions are at least the following loci: nucleotides 21549529 to 21645346 of chromosome 8; nucleotides 40962149 to 41065386 of chromosome 17; nucleotides 8559665 to 8890849 of chromosome 8; nucleotides 113139327 to 113242481 of chromosome 13; nucleotides 131265453 to 131978646 of chromosome 10; nucleotides 136469715 to 136659848 of chromosome 8; nucleotides 135490030 to 135725292 of chromosome 8; nucleotides 83637442 to 84746935 of chromosome 10; nucleotides 90640025 to 90775542 of chromosome 10; nucleotides 90579658 to 90611732 of chromosome 10; nucleotides 8175257 to 8239257 of chromosome 8; nucleotides 7305275 to 7754237 of chromosome 8; nucleotides 8993763 to 9009152 of chromosome 8; nucleotides 43511808 to 43586893 of chromosome 19; nucleotides 7286415 to 7740105 of chromosome 8; nucleotides 191625 to 256814 of chromosome 13; nucleotides 48972117 to 49147744 of chromosome 22; nucleotides 149570056 to 149577787 of chromosome 7; nucleotides 149535508 to 149564568 of chromosome 7; nucleotides 47158517 to 47571342 of chromosome 22; nucleotides 149473130 to 149531053 of chromosome 7; nucleotides 12869772 to 12887284 of chromosome 8; nucleotides 12579405 to 12612992 of chromosome 8; nucleotides 88744089 to 88781786 of chromosome 16; nucleotides 88003623 to 88601574 of chromosome 16; nucleotides 90033620 to 90343082 of chromosome 10; nucleotides 88636788 to 88729495 of chromosome 16; nucleotides 9413444 to 9639856 of chromosome 8; nucleotides 72937384 to 73024522 of chromosome 3; nucleotides 87863628 to 87970112 of chromosome 16; nucleotides 111530886 to 111567416 of chromosome 13; nucleotides 42607779 to 42623929 of chromosome 8; nucleotides 11141999 to 11189695 of chromosome 8; nucleotides 90965693 to 90967071 of chromosome 10; nucleotides 90346518 to 90537999 of chromosome 10; nucleotides 116638561 to 117072975 of chromosome 9; nucleotides 42396938 to 42408140 of chromosome 8; nucleotides 11994676 to 12051624 of chromosome 8; nucleotides 11921897 to 11973025 of chromosome 8; nucleotides 1201709 to 1295162 of chromosome 5; nucleotides 1317999 to 1345002 of chromosome 5; nucleotides 1392904 to 1445543 of chromosome 5; nucleotides 60697516 to 60777810 of chromosome 20; nucleotides 42010463 to 42065194 of chromosome 8; nucleotides 42249278 to 42397068 of chromosome 8;

(c) determining a plurality of copy number calls in the genome regions;
(d) intersecting the plurality of copy number calls with a reference gene list, to obtain a plurality of Copy Number Alterations (CNA) calls for each gene;
(e) generating a CNA tumour profile based on the plurality of CNA calls;
(f) comparing the CNA tumour profile to a reference profile of recurring cancer patients and a reference profile of nonrecurring cancer patients;
(g) calculating a plurality of statistical distances between the CNA tumour profile and the reference profile of recurring cancer patients and the reference profile of nonrecurring cancer patients;

wherein the statistical distance between the CNA tumour profile and the reference profile of recurring cancer patients and the reference profile of nonrecurring cancer patients is associated with the risk of cancer recurrence following the cancer therapy of the patient.

* * * * *